United States Patent [19]

Lis et al.

[11] Patent Number: 5,051,423

[45] Date of Patent: Sep. 24, 1991

[54] DERIVATIZED ALKANOLAMINES AS CARDIOVASCULAR AGENTS

[75] Inventors: Randall E. Lis, Stanhope, N.J.; William C. Lumma, Jr., Pennsburg, Pa.; Thomas K. Morgan, Jr., Morris Plains, N.J.; Klaus Nickisch, Berlin, Fed. Rep. of Germany; Ronald A. Wohl, Morris Plains, N.J.

[73] Assignee: Schering AG, Berlin, Fed. Rep. of Germany

[21] Appl. No.: 218,195

[22] Filed: Jul. 13, 1988

[51] Int. Cl.$^5$ .............. A61K 31/495; A61K 31/415; C07D 403/10; C07D 233/60
[52] U.S. Cl. .................. 514/252; 514/255; 514/399; 514/605; 544/370; 544/386; 544/391; 544/393; 544/394; 548/341; 564/99
[58] Field of Search .............. 544/386, 394, 370, 391; 514/255, 252, 399, 605; 548/341; 564/99

[56] References Cited

U.S. PATENT DOCUMENTS

| | | | |
|---|---|---|---|
| 3,701,777 | 10/1972 | Edenhofer et al. | 544/394 |
| 3,816,516 | 6/1974 | Cox et al. | 260/501.17 |
| 4,034,106 | 7/1977 | Smith | 424/304 |
| 4,438,128 | 3/1984 | Wiedemann et al. | 544/317 |

FOREIGN PATENT DOCUMENTS

| | | |
|---|---|---|
| 68669 | 1/1983 | European Pat. Off. |
| 257864 | 3/1988 | European Pat. Off. |

OTHER PUBLICATIONS

Gupta et al., Chem. Abst. 87-167976f (1977).
Oshiro et al., Chem. Abst. 88-50671g (1978) "3,4-Dihydrocarbostyril Derivatives".
Oshiro et al., Chem. Abst. 90-54841b (1979) "3,4-Dihydrocarbostyril Derivatives".
Otsuka Pharmaceutical Co., Ltd. Chem. Abst. 94-58490s (1981), "Styrene Derivatives as Antihistamines".
Kemp et al., Chem. Abst. 109-6547z (1988) "Preparation of Sulfonamidoaralkylpiperazines as Antiarrhythmics".

*Primary Examiner*—Cecilia Shen
*Attorney, Agent, or Firm*—Elizabeth A. Bellamy; John L. White; I. William Millen

[57] ABSTRACT

Novel derivatized alkanolamines of the following structural formula

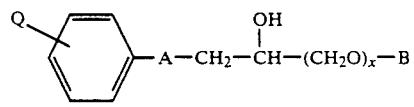

are described as useful cardiovascular agents. Most especially described is their usefulness as cardiovascular agents exhibiting an antiarrhythmic effect. Said antiarrhythmic effect is of a combination Class II/Class III variety. Pharmaceutical formulations containing such compounds are also described.

36 Claims, No Drawings

DERIVATIZED ALKANOLAMINES AS CARDIOVASCULAR AGENTS

FIELD OF INVENTION

This invention relates to novel derivatized alkanolamines and their use as cardiovascular agents. More specifically, it deals with alkanolamines derivatized by at least imidazol-1-ylphenyl or alkylsulfonaminophenyl moieties, and their pharmaceutically acceptable salts. In the cardiovascular aspect compounds have been found especially to be antiarrhythmic agents possessing a combination Class II/Class III activity. The invention also relates to pharmaceutical compositions containing such compounds and their usefulness in cardiovascular therapy.

GENERAL DESCRIPTION OF THE INVENTION

Composition-of-Matter Aspect

In its composition-of-matter aspect this invention relates to novel derivatized alkanolamines and their pharmaceutically acceptable salts. Particularly, this invention relates to the novel compounds defined by the following Formula I:

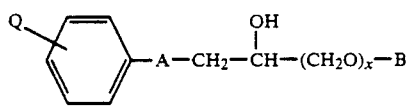

In the foregoing Formula I
Q is defined as $(C_1-C_4)-SO_2-NH-$ or

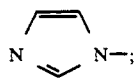

x is the integer 0 or 1;
A is defined as

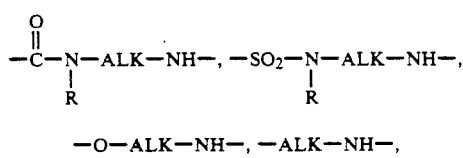

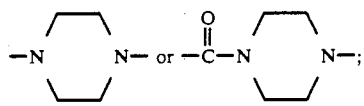

B is

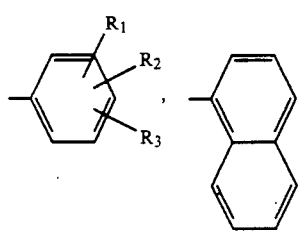

-continued

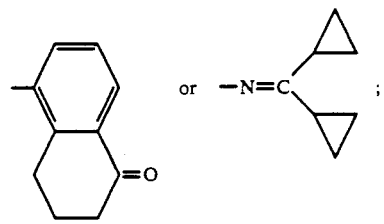

ALK is $-(CH_2)_r-$ or

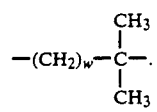

R is hydrogen, lower alkyl, 2-propenyl or loweralkoxyloweralkyl. $R_1$, $R_2$, and $R_3$ are the same or different and selected from hydrogen, lower alkyl, lower alkoxy, 2-propenyl, 2-propenyloxy, loweralkoxyloweralkyl, halogen.

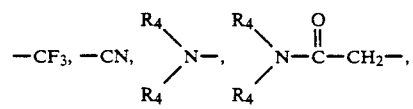

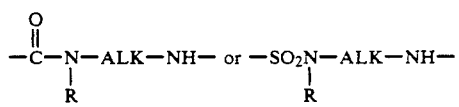

r is an integer of 1-4;
w is an integer of 1-3;
p is an integer of 1-3 and
t is an integer of 2-5.

$R_4$ is hydrogen or lower alkyl; and the pharmaceutically acceptable salts thereof, with the provisos that:

a) when A is

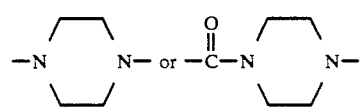

then Q cannot be $(C_1-C_4)-SO_2NH-$;

b) Q cannot be ortho to the "A" attachment and further when Q is $(C_1-C_4)-SO_2NH-$, it must be para to the A attachment;

c) when A is $-N\diagdown\diagup N-$ or $-\overset{O}{\overset{\|}{C}}-N\diagdown\diagup N-$ then x must be the integer 1;

d) when A is $-O-ALK-NH-$, then r cannot be the integer 1;

e) when x =0 then B cannot be

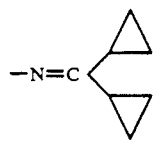

and f) when Q is $(C_1-C_4)-SO_2NH-$ and A is ALK then x must be the integer 1.

As indicated, contemplated as part of this invention are the pharmaceutically acceptable salts of the compounds of Formula I. Useful acids for this purpose include both inorganic and organic acids such as hydrochloric, hydrobromic, sulfuric, phosphoric, acetic, propionic, benzoic, naphthoic, oxalic, succinic, maleic, malic, adipic, lactic, tartaric, citric, salicylic, methanesulfonic, and p-toluenesulfonic acids.

It is to be understood that the definition of the compounds of Formula I encompasses all possible stereoisomers and mixtures thereof which possess the activity discussed below. In particular, it encompasses racemic modifications and any optical isomers which possess the indicated activity.

In the above Formula I the term lower alkyl shall refer to a straight or branched chain of from 1 to 4 carbon atoms, lower alkoxy shall refer to a straight or branched chain of from 1 to 4 carbon atoms. The term l.oweralkoxyloweralkyl shall be taken to mean a straight or branched chain alkoxy/alkyl of from 1 to 4 carbon atoms. The term halogen shall be taken to mean fluorine, chlorine, bromine or iodine.

Preferred classes of compounds embodied by this invention are those of the above general Formula I and having the following characteristics:

a) when A is —O—ALK—NH— and Q is $(C_1-C_4)-SO_2NH-$;

b) when A is —O—ALK—NH— and Q is

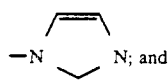

and c) when A is

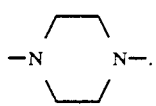

In addition to the compounds exemplified in the Examples section, the following are representative of still further aspects of the invention.

1. N-[4-[2-[[2-hydroxy-3-[4-(2-methoxyethyl)phenoxy]-propyl]amino]ethoxy]phenyl]methanesulfonamide.
2. N-[4-[3-[[2-hydroxy-3-[4-[(methylsulfonyl)amino]-phenoxy]propyl]amino]-3,3-dimethylpropoxy]-phenyl]propanesulfonamide.
3. N-[4-[2-[[3-[[[bis(cyclopropyl)methyl]imino]oxy]-2hydroxypropyl]amino]ethoxy]phenyl]ethanesulfonamide.
4. N-[4-[2-[[-3-(5,6,7,8-tetrahydro-5-oxo-1-naphthalenyl-oxy)-2-hydroxypropyl]amino]ethoxy]phenyl]-butanesulfonamide.
5. N-[4-[3-[[2-hydroxy-2-(1-naphthalenyl)ethyl]amino]-propoxy]phenyl]methanesulfonamide.
6. N-[4-[2-[[3-(3,4,5-triethoxyphenoxy)-2-hydroxy-propyl]-amino]ethoxy]phenyl]methanesulfonamide.
7. N-[2-[[3-[[[bis(cyclopropyl)methyl]imino]oxy]-2-hydroxypropyl]amino]ethyl]-4-[(ethylsulfonyl)amino]benzenesulfonamide.
8. N-[2-[[2-hydroxy-3-(1-naphthalenyloxy)propyl]-amino]ethyl]-4-[(methylsulfonyl)amino]benzenesulfonamide.
9. N-[2-[[3-[4-(2-ethoxyethyl)phenoxy]-2-hydroxypropyl]amino]ethyl]-4-(1H-imidazol-1-yl)benzenesulfonamide.
10. N-[4-[[2-hydroxy-2-(1-naphthalenyl)ethyl]amino]-4,4-dimethylbutyl]-4-(1H-imidazol-1-yl)-N-propyl-benzenesulfonamide.
11. N-[2-[[3-[[[bis(cyclopropyl)methyl]imino]oxy]-2-hydroxypropyl]amino]ethyl]-4-[1H-imidazol-1-yl]benzenesulfonamide.

PROCESS ASPECT

In general, the compounds of this invention may be prepared by various reactants and processes known in the art. Illustrative but not limiting as the reactants and processes utilized for the preparation of the compounds of the invention are the following Schemes A–H and J:

As depicted in Scheme A, treating methyl aminobenzoates 1 under typical Debus conditions (NH$_4$OH, formaldehyde and glyoxal) affords methyl imidazolylbenzoates 2. Reaction of methyl aminobenzoates 1 with various alkylsulfonyl chlorides in pyridine and methylene chloride, usually at about 0° C., gives methyl alkylsulfonylaminobenzoates 2. Compounds 2, when treated with aqueous sodium hydroxide, give the sodium salts 3. Acid chloride formation follows when the sodium salt 3 is treated with thionyl chloride (neat) or in refluxing toluene. Amides 5 are prepared when acid chlorides 4 are treated with 1-benzylpiperazine in a solvent such as tetrahydrofuran. Hydrogenolysis of the benzyl group occurs when the amides 5 are treated with hydrogen gas and a catalyst such as palladium on carbon. Common solvents for this hydrogenolysis are water, ethanol, methanol and various mixtures thereof. Compounds 7 of this invention are prepared when amide 6 is mixed with known in the art epoxides in methanol. Compounds 9 are prepared by treating amides 6 with α-haloketones and Huenigs base in acetonitrile and subsequently reducing the ketone moiety of 8 under standard hydrogenation conditions (H$_2$, Pd-C, MeOH/H$_2$O).

Scheme B summarizes the process for preparing compounds 13 and 15 where ALK=CH$_2$. Treatment of aminobenzonitriles 10 under typical Debus conditions give imidazolylbenzonitriles 11. Aminobenzonitriles 10 can be alkylsulfonylated giving 11, using various alkylsulfonylchlorides in pyridine and methylene chloride. Reduction of the cyano moiety of 11 using hydrogen gas (~50 psi) and a Raney-Nickel catalyst in ammonia/methanol produces alkylamines 12. Treating 12 with known in the art epoxides in a solvent such as methanol gives compounds 13. Compounds 15 are prepared by reacting 12 with α-halo ketones and Huenig's base in acetonitrile and subsequently reducing the ketone moiety of 14 under standard hydrogenation conditions (H$_2$, Pd-C, MeOH/H$_2$O).

Scheme C summarizes the preparation of compounds 13 and 15 where ALK has the meaning described above in the specification and claims section of this invention. Generally nitrophenalkyl halides 16 are treated with sodium phthalimide in a solvent such as dimethylformamide and give nitrophthalimides 17. Reduction of the nitro moiety by the method of Bellamy (SnCl₂, EtOH) gives aminophthalimides 18 after work up. Imidazole formation via the Debus reaction (NH₄OH, formaldehyde, glyoxal) follows to give 19. Alkylsulfonylamino derivatives 19 are prepared by treatment of 18 with various alkylsulfonyl chlorides in pyridine and methylene chloride. Cleavage of the phthalimide moiety of 19 using hydrazine hydrate in refluxing ethanol yields alkylamines 12. Compounds 12 are employed to produce 13 and 15 using the general method outlined in Scheme B.

Preparations of compounds 24 and 26 of this invention are summarized in Scheme D. Treatment of 1-fluoro-4-nitrobenzene and 1-benzylpiperazine in acetonitrile with potassium carbonate affords nitrophenylpiperazine 20. Reduction of the nitro group using tin chloride in ethanol gives aminophenylpiperazine 21. When 21 is stirred with a mixture of ammonia, formaldehyde and glyoxal (Debus conditions) imidazole 22 is formed. Treating 21 with various alkylsulfonic anhydrides in a solvent such as acetonitrile produces alkylsulfonylamides 22. Hydrogenolysis of the benzyl group of 22 is carried out using standard conditions (H₂, Pd-C, EtOH/H₂O) and yields 23. Reaction of 23 with known in the art epoxides in mixtures of methanol and water give compounds 24. Compounds 26 are prepared by treating 23 with α-haloketones and Huenig's base in acetonitrile and subsequently reducing the ketone moiety of 25 using standard reduction conditions (H₂, Pd-C, MeOH/H₂O).

The corresponding 3-imidazolyl derivatives 31 and 33 are prepared by analogous synthetic methods to those used for 24 and 26 via Scheme E. The only difference is that compound 27 is produced from the treatment of 3-nitroaniline with N,N-bis(2-chloroethyl)benzylamine hydrochloride in ethanol containing potassium carbonate. Compound 27 is carried through the same synthetic sequences as 20 (Scheme D) and provides compounds 31 and 33 of this invention.

The synthetic sequences for preparing compounds 37 and 39 is summarized in Scheme F. Imidazolyl-phenols 34 can be alkylated with various chloroalkylamines or chloroalkylbenzylamines with sodium hydride in dimethylformamide to give imidazole-amines 35 and 36, respectively. Treatment of 35 with various epoxides in methanol/water affords compounds 37. Reaction of imidazole-amines 36 with α-haloketones and Huenigs base in acetonitrile yields imidazole-ketones 38. Standard reduction of 38 (H₂, Pd-C, MeOH/H₂O) gives compound 39 of this invention.

Compounds 45 and 47 of this invention can be synthesized by the sequence shown in Scheme G. Nucleophilic aromatic substitution of 1-fluoro-4-nitrobenzene with various dibenzylaminoalcohols using sodium hydride in dimethylformamide and tetrahydrofuran affords nitrodibenzylamines 40. Reduction of the nitro group (SnCl₂, EtOH) followed by alkylsulfonylation in acetonitrile yields dibenzylamines 42. Monodebenzylation of 42 can be achieved under standard hydrogenolysis conditions (H₂, Pd-C, EtOH/H₂O) to give benzylamines 43. Complete debenzylation of 42 can be accomplished under more vigorous conditions (H₂, Pd(OH)₂, HOAc, ~50 psi) and affords amines 44. Amines 43 and 44 can be carried through the same synthetic sequences as amines 36 and 35 (Scheme F) to give compounds 45 and 47 of this invention.

Dibenzylamines 49 can be prepared by reacting various dibenzyldiamines with either benzenesulfonyl chlorides or benzoyl chlorides 48 in a solvent such as tetrahydrofuran (Scheme H). Compounds 49 can be carried through the same sequences as compounds 42 (Scheme G) to produce compounds 52 and 54 of this invention.

An alternate way of preparing 52 follows from Scheme J. Methyl imidazolylbenzoates 55 can be heated with various alkanediamines to give amines 50. Treating 50 with epoxides known in the art yields compounds 52 of this invention.

In general the methods for preparing the optically active enantiomers of the compounds of Formula I follow standard procedures. For instance, to produce the compounds of Formula I wherein x is the integer 1, the corresponding epoxides are formed from the optically active epicholorohydrins or tosylates. In the instance where x is the integer 0 the compounds, via one procedure, are prepared from the corresponding racemates by classical resolution procedures i.e., optically active acids forming diastereomeric salts which are separated then converted to the free bases to produce the corresponding enantiomers.

SCHEME A

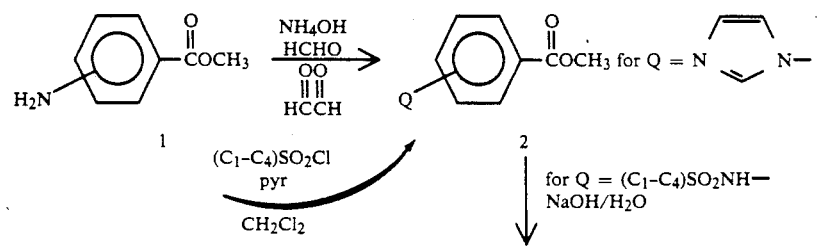

SCHEME A
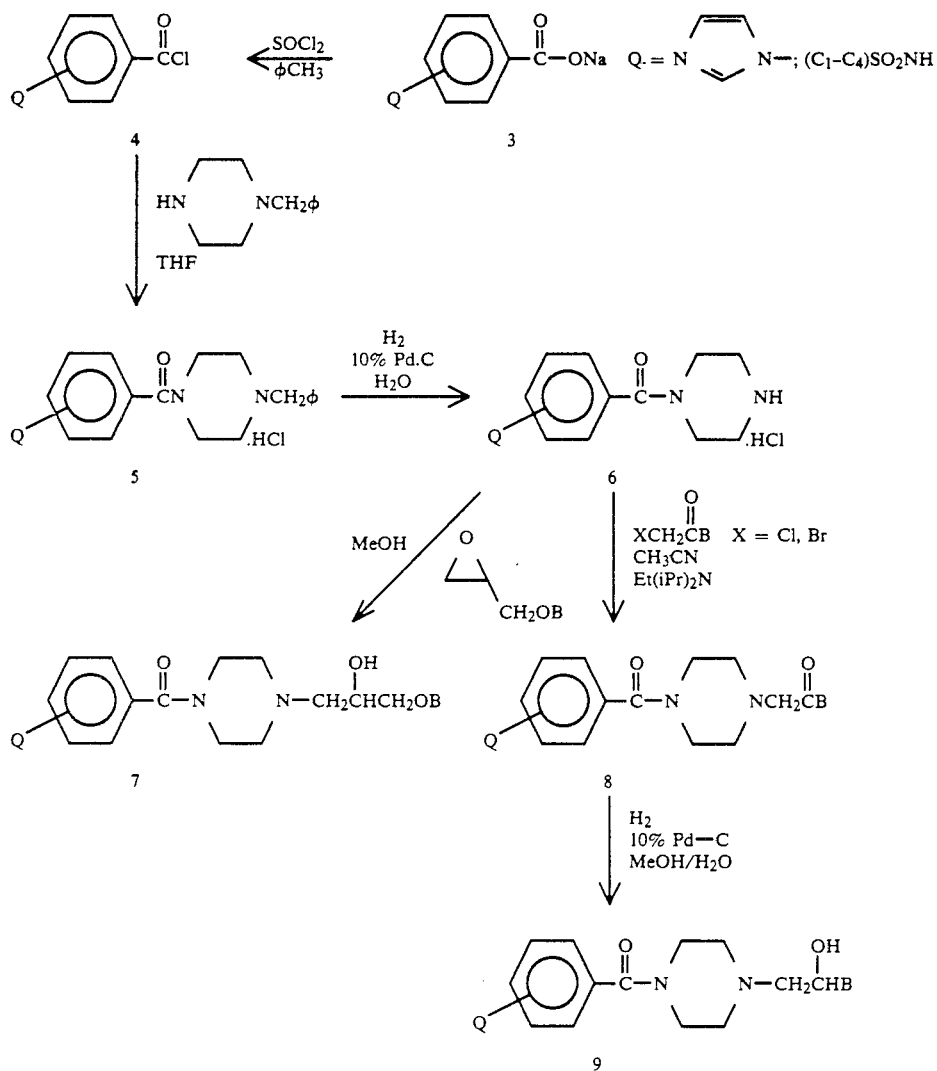
SCHEME B
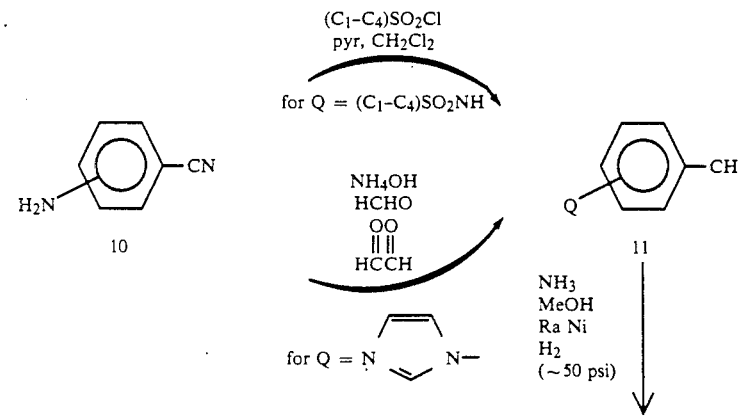

-continued
SCHEME B
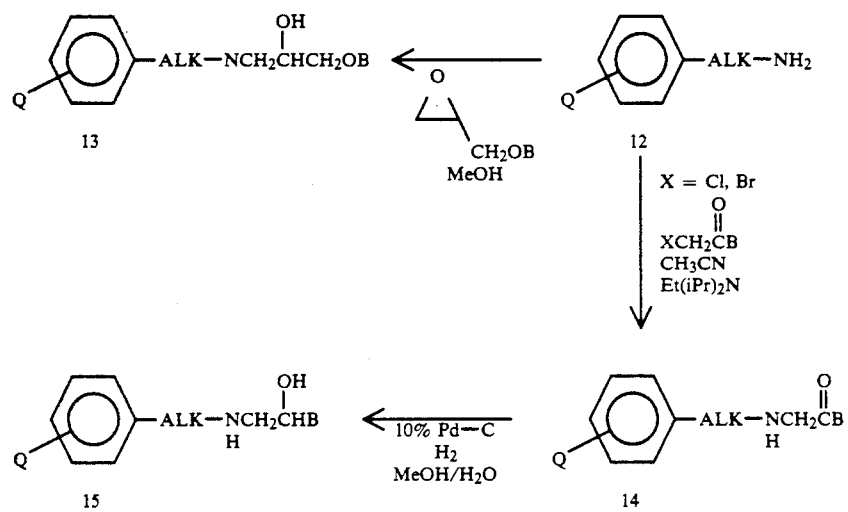
SCHEME C
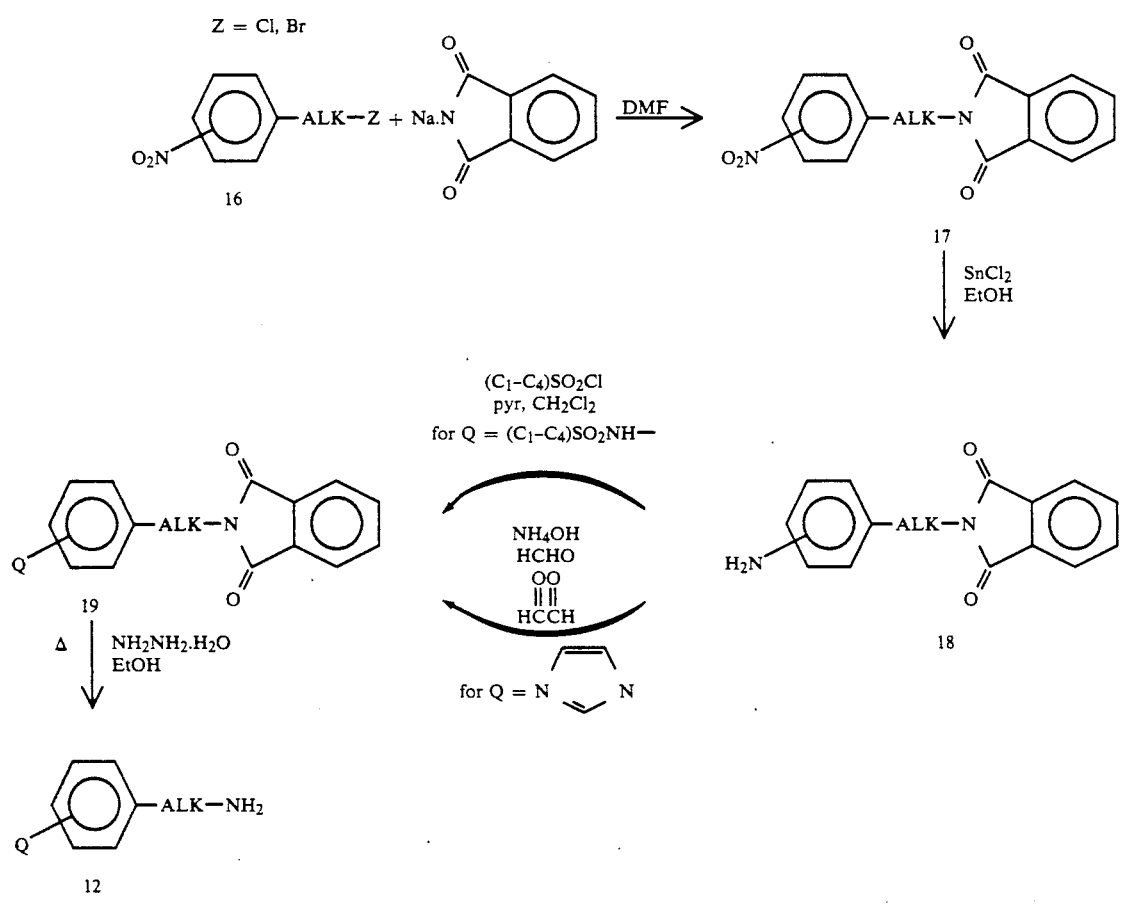

SCHEME D
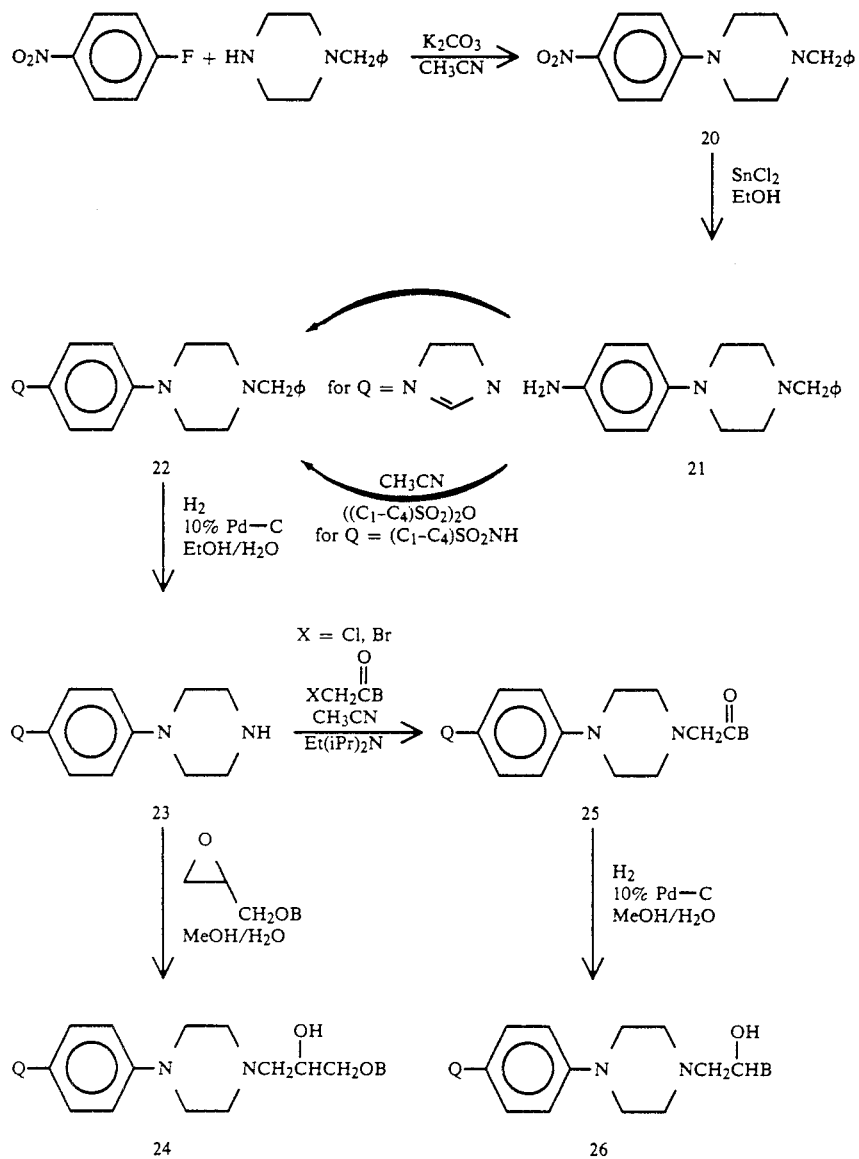
SCHEME E
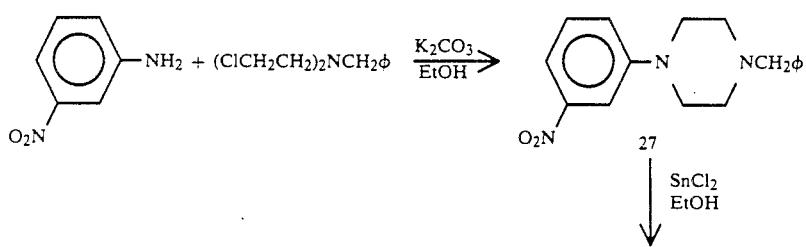

SCHEME E
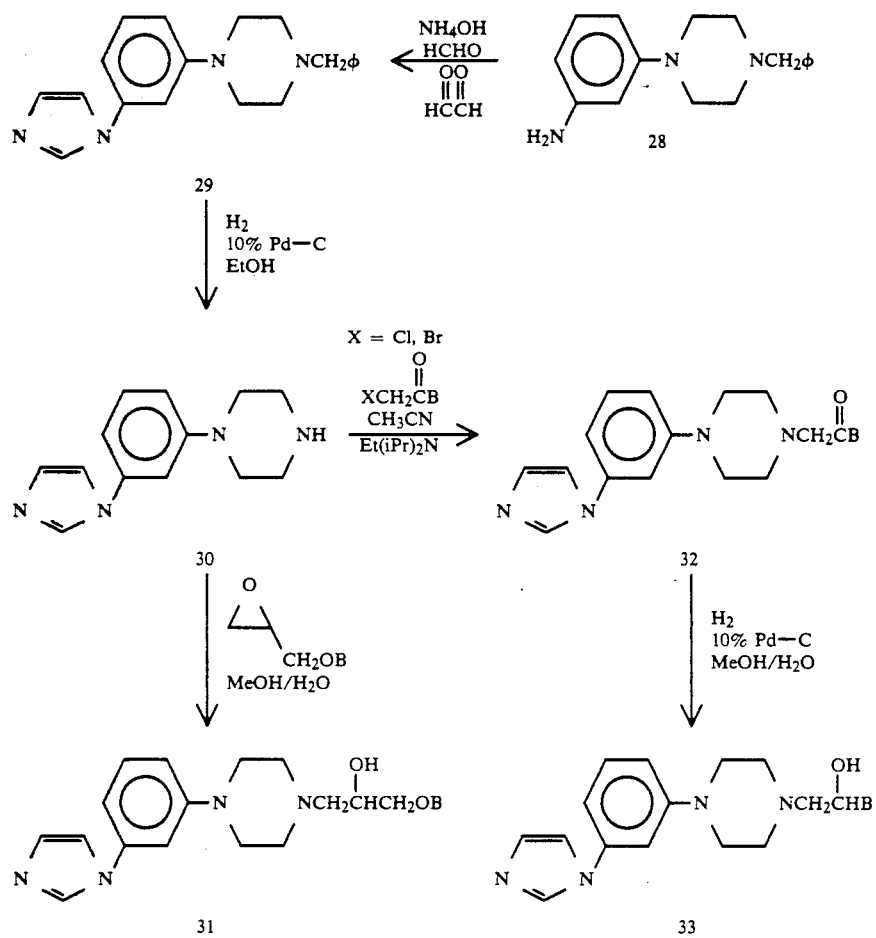
SCHEME F
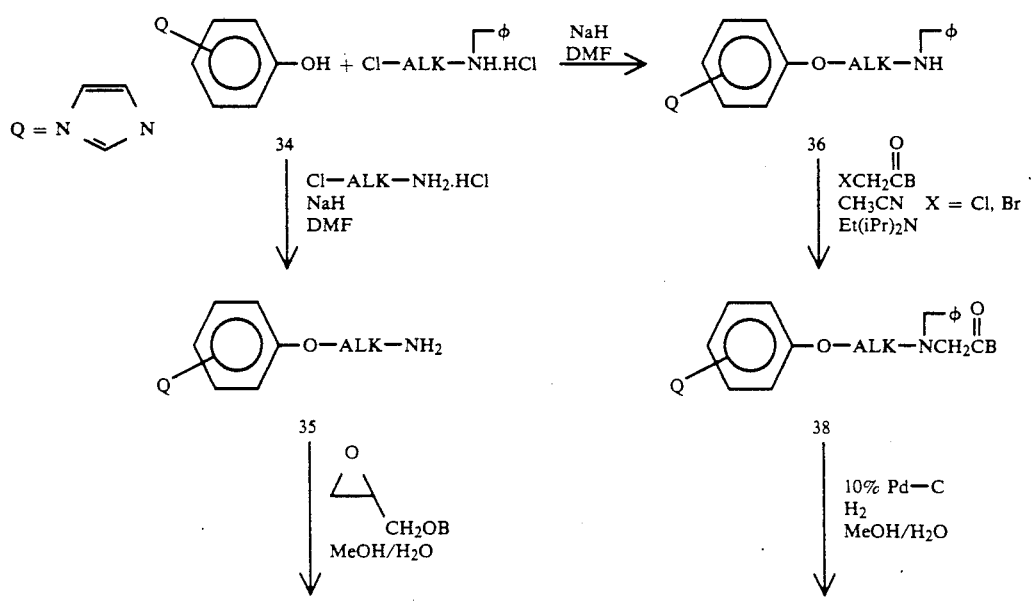

-continued
SCHEME F
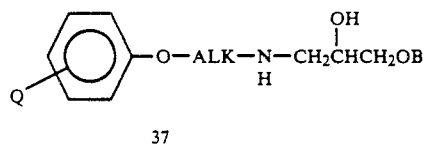
37
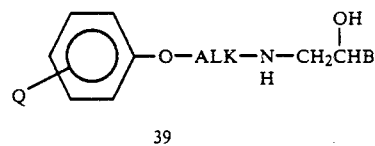
39
SCHEME G
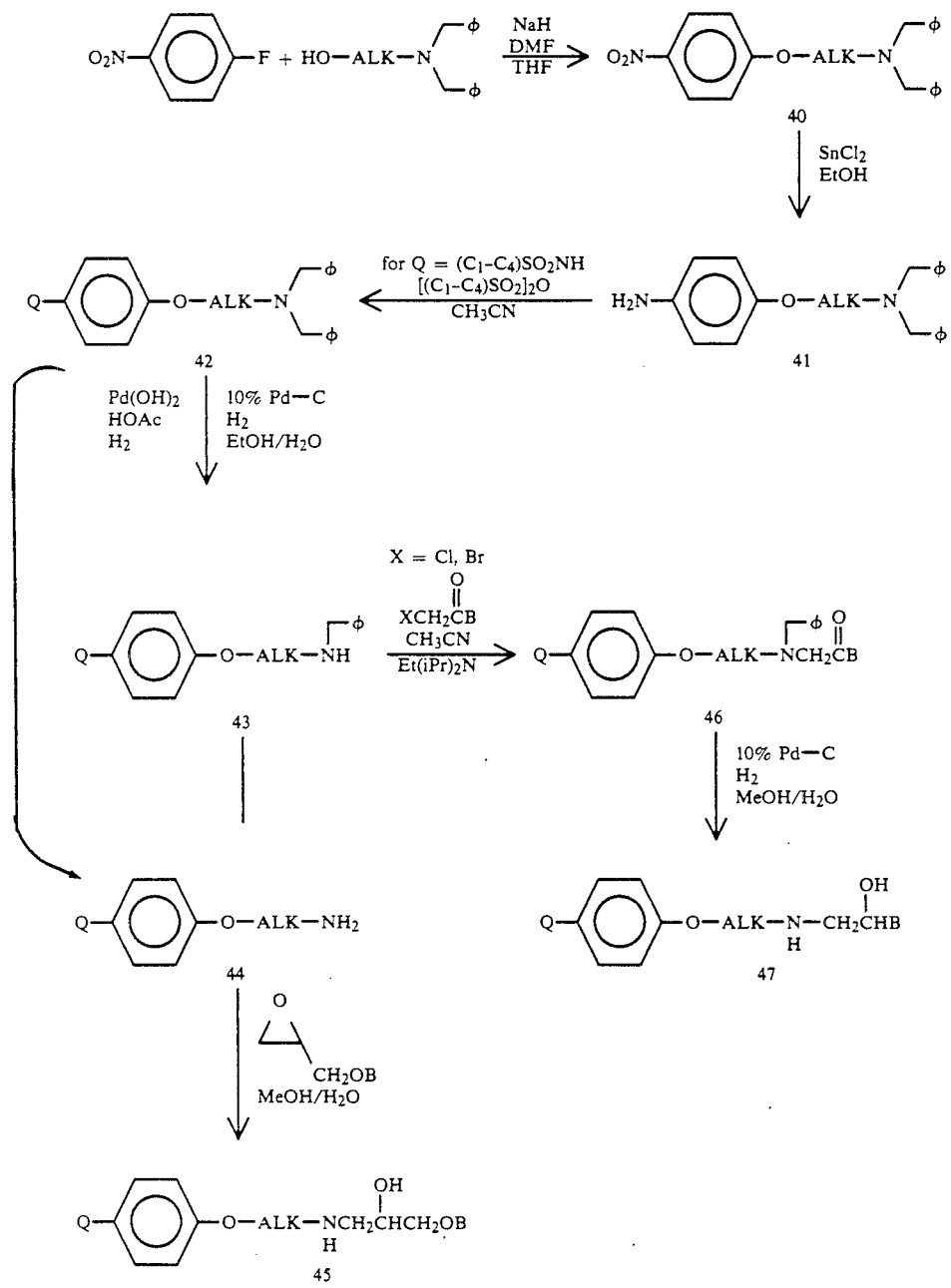

SCHEME H

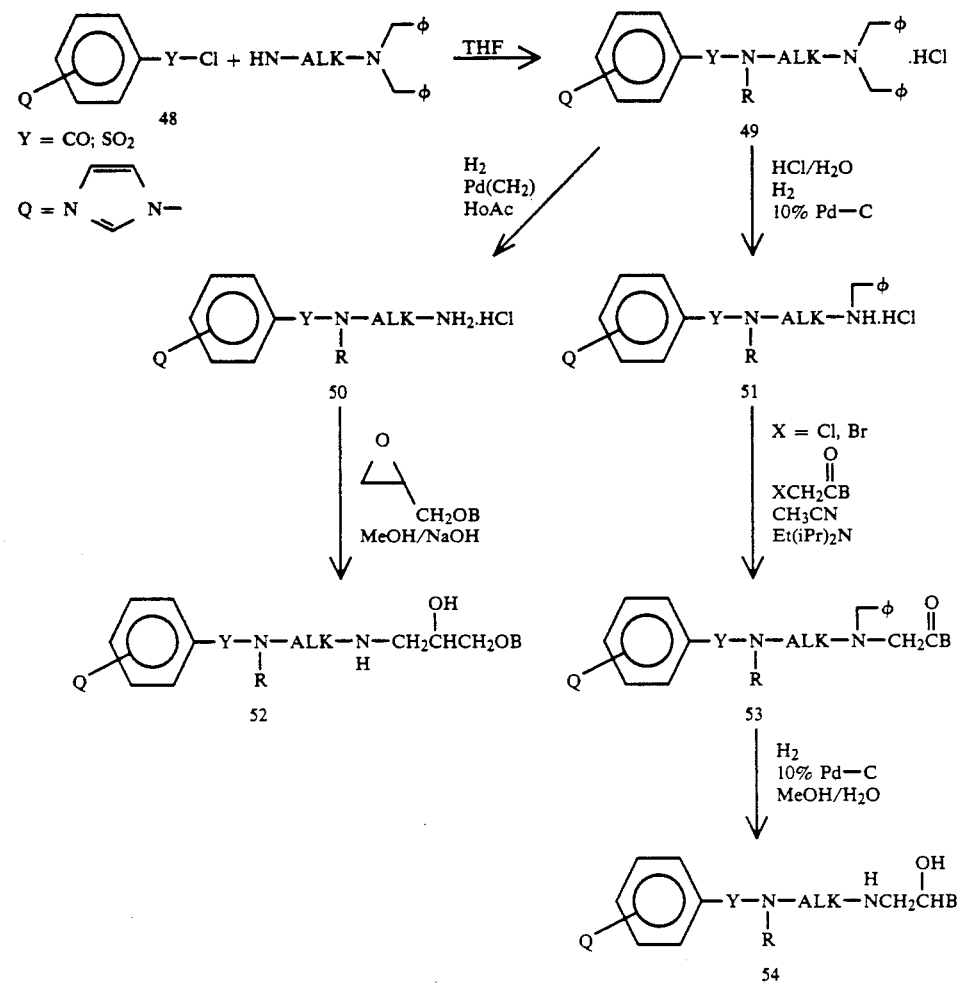

SCHEME J

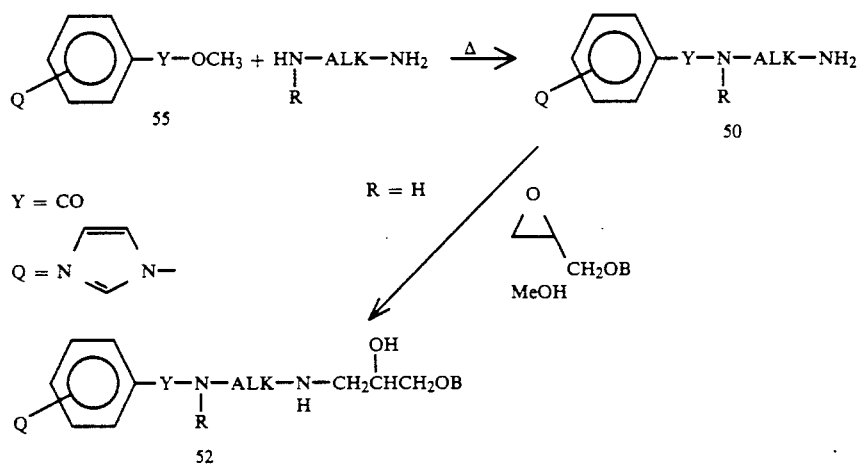

METHOD-OF-USE AND PHARMACEUTICAL COMPOSITION ASPECT

The novel alkanolamines of this invention derivatized by at least a imidazol-1-ylphenyl or alkylsulfonylaminophenyl moiety and their pharmaceutically acceptable salts are cardiovascular agents. Most especially within the aegis of cardiovascular pharmacology, these compounds have been specifically designed to provide a combination beta-adrenergic blockade with electrophysiologic activity to selectively prolong cellular refractoriness. According to the Vaughan Williams classification, such agents would have Class II/Class III antiarrhythmic effect. Such combination contains those therapeutic effects attributed to Class II and Class III antiarrhythmic agents singly.

In the Vaughan Williams classification of antiarrhythmic agents, Class II agents are the β-adrenergic blocking agents, which so called β-blockers decrease the sensitivity of the cardiac tissue to catecholamines. The catecholamines in excess can increase the electrical instability of the heart. Class II agents are exemplified by propranolol, metoprolol, nadolol, timolol, atenolol, sotalol, acebutolol and nipradilol. The Class III agents prolong the action potential duration of the heart thus increasing the time interval in which the heart is unexcitable (refractory period) without slowing conduction or changing the excitability of the cardiac cells. These agents have little or no effect on conduction, in fact, they are quite independent of conduction. Such agents are exemplified in the literature by bretylium, amiodarone, clofilium, melperone and sematilide (the latter compound developed in these laboratories).

Several investigators have demonstrated that the arrhythmia responsible for sudden cardiac death is ventricular fibrillation (VF). VF has been shown to occur via a reentrant mechanism. Reentrant ventricular arrhythmias can occur as a result of abnormalities in conduction and/or refractoriness. In a reentrant arrhythmia, a single cardiac impulse follows a circular pathway, allowing repeated excitation of the same tissue. One approach to the abolition of such reentrant arrhythmias is to further prolong the refractory period of cardiac cells, such that the impulse, upon returning to its point of origin, is met with refractory tissue and propagation of the impulse is stopped. This is clearly the therapeutic rationale behind the development of agents possessing Class III activity.

Reentrant arrhythmias often are initiated or "triggered" by an appropriately timed premature impulse. In patients following myocardial infarction, excessive catecholamine levels may be responsible for triggering many arrhythmias which may be associated with sudden cardiac death. In fact, the results of several large, multi-center trials have shown that beta-adrenergic blockers can reduce mortality from sudden cardiac death in post-infarction patients. Presumably, beta-blockers work by decreasing the sensitivity of the heart to catecholamines, and thereby decrease the potential "triggering" event which leads to reentrant ventricular arrhythmias. The overall decrease in mortality from these studies is approximately 25%, suggesting that beta-adrenergic blockade when used alone offers no beneficial antiarrhythmic effect in the remaining majority of post-infarction patients. Clinical data such as these highlight the multiple etiologies present in patients dying of sudden cardiac death and the need for a more "broad spectrum" approach.

One broad spectrum approach is to produce an agent with both Class II and Class III properties. Several investigators have shown that an increase in sympathetic tone to the heart will shorten refractoriness, an action which can be blocked by beta-adrenergic antagonists. Preliminary data using the selective Class III agent clofilium have shown that its Class III actions are blunted in the setting of enhanced sympathetic tone (Sullivan and Steinberg, 1981). Furthermore preliminary studies performed in conscious dogs in these laboratories suggest a synergistic effect between inhibition of beta-receptors and prolongation of refractoriness. In pilot studies utilizing programmed electrical stimulation (PES) techniques to induce reentrant arrhythmias, a sub-therapeutic dose of sematilide was administered and shown not to be efficacious. Subsequent administration of a beta-blocking dose of propranolol (0.5 mg/kg, i.v.) was shown to protect the heart from PES-induced arrhythmias. Previous studies in these laboratories have demonstrated that propranolol when used alone is not efficacious in this model. In animals receiving the combination therapy, ventricular refractory period increased 8% following sematilide and 18% with the addition of propranolol. Propranolol, when used alone at this dose, had no effect on refractoriness. These data suggest a synergistic action between Class III and Class II agents and that modulation of beta-adrenergic tone can enhance the Class III properties of certain agents.

Sotalol can be considered the prototype drug for an agent with both Class II and Class III activity. Experimental and clinical data suggest that the beta-blocking effect of sotalol begins at doses lower or equivalent to doses which produce its Class III actions. Thus, the compounds of this invention are designed to have a more potent Class III action relative to their Class II potency in order to demonstrate a distinct advantage in the setting of reentrant ventricular arrhythmias.

The compounds of this invention have been tested for their Class III activity via in vitro electrophysiologic testing utilizing standard intracellular microelectrode techniques in the canine cardiac Purkinje fiber. They were then tested for reasonable B-adrenergic blocking activity as measured in the in vitro screens of isolated papillary muscle (inhibition of the inotropic response to epinephrine) and the beta-adrenergic binding screen (displacement of radiolabelled dihydroalprenolol). They were then assessed in the in vivo model of the pentobarbital anesthetized dog in which the compound was administered intraduodenally and its Class III (increase in functional refractory period) and Class II (inhibition of isoproterenol response) effects were monitored.

The compounds of this invention exemplified by N-[4-[4-[2-hydroxy-3-(2-methylphenoxy)propyl]piperazin-1-yl]phenyl]methanesulfonamide, N-[4-[2-hydroxy-3-[[2-[4-(1H-imidazol-1-yl)phenoxy]amino]propoxy]-phenyl]methanesulfonamide and N-[4-[1-hydroxy-2-[[2-[4-(1H-imidazol-1-yl)phenoxy]ethyl]amino]ethyl]-phenyl]methanesulfonamide have been analyzed in the foregoing biological procedures and provide the combination Class II/III antiarrhythmic effects. In essence, the physician has been provided with a simple chemical entity providing 2 effects thereby mitigating the problems of multiple drug therapy, e.g. side effects, metabolic problems, drug interactions, etc. and the problems in patient compliance—different drugs, different therapeutic regimens.

The compounds whilst preferably utilized in the treatment of mammalian arrhythmias and most specifically used in the treatment of mammalian arrhythmias in need of combination Class II/III effects, possess some general cardiovascular properties. Some of the compounds may, due to the level of Class II effects, exhibit an anti-hypertensive effect.

In general, the compounds of this invention may be administered orally or parenterally. The dosage administered will depend on the subject being treated, the route of administration and the type and severity of the arrhythmias being prevented or reduced.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention for example, N-[4-[4-[2-hydroxy-3-(2-methylphenoxy)propyl]piperazin-1-]phenyl]methanesulfonamide, N-[4-[2-hydroxy-3-[[2-[4-(1H-imidazol-1-yl)phenoxy]ethyl]amino]propoxy]phenyl]methanesulfonamide or N-[4-[1-hydroxy-2-[[2-[4-(1H-imidazol-1-yl)phenoxy]ethyl]amino]ethyl]phenyl]methanesulfonamide in the amount of about 1 to about 500 mg. Such formulation can be administered orally at the rate of about 1 to 4 capsules per day or more often as needed, depending upon the particular condition and subject being treated.

For parenteral administration a compound of this invention can be formulated as an intramuscular or intravenous medicament but is not limited thereto. In the case of treatment of a patient suffering from severe cardiac arrhythmias, it may be desirable to administer a compound of the invention by intravenous slow bolus in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or a saline solution, buffered aqueous solutions as well as dispersing and surface active agents if necessary. A typical formulation suited to intravenous or intramuscular administration may contain one of the compounds of this invention such as N-[4-[4-[2-hydroxy-3-(2-methylphenoxy)propyl]piperazin-1-]phenyl]methanesulfonamide in the amount of about 50 to 150 mg and a solubilizing agent and sufficient sterile water to bring the volume to about 5 ml-100 ml. Such formulation can be infused at a constant rate or injected one to four times per day or more often depending upon the particular condition of the subject being treated.

It is further contemplated that the compounds of this invention may be formulated into sublingual lozenges or impregnated into fabric appliques for a type of transdermal application.

The invention described hereinabove is illustrated below in the Preparations and Examples, which, however, are not to be construed as limiting the scope of this invention.

PREPARATIONS

Preparation 1

N-[2-[4-(1H-Imidazol-1-yl)phenoxy]ethyl]propionamide

To 25 g (0.25 mol) of 2-ethyl-4,5-dihydrooxazole add 10.0 g (62 mmol) of 4-(1H-imidazol-1-yl)phenol. Reflux the reaction mixture. Monitor the progress of the reaction by thin-layer chromatography on silica gel (9:1, $CH_2Cl_2$:MeOH). Upon completion of the reaction remove the excess starting material by distillation, add ethyl acetate, and wash the solution with 2 N NaOH. Dry the organic layer over anhydrous $Na_2SO_4$. Remove the drying agent by filtration and remove the solvent in vacuo. Recrystallization from ethyl acetate-hexane affords the title compound.

NMR (DMSO-$d_6$) $\delta = 1.01$(t,3), 2.12(q,2), 3.44(q,2), 4.04(t,2), 7.09(d,2), 7.09(s,1), 7.57(d,2), 7.67(s,1), 8.08(brt,1) and 8.16(s,1) ppm.

Preparation 2

2-[4-(1H-Imidazol-1-yl)phenoxy]ethanamine dihydrochloride

To 40 mL of 2M aqueous hydrochloric acid add 10.3 g (39 mmol) of N-[2-[4-(1H-imidazol-1-yl)phenoxy]ethyl]propionamide. Reflux the reaction mixture. Monitor the progress of the reaction by thin-layer chromatography on silica gel (9:1, $CH_2Cl_2$:MeOH). Upon completion of the reaction, remove the solvent in vacuo and triturate with isopropanol. Recrystallization of the resulting solid from ethanol affords the title compound.

NMR (DMSO-$d_6$) $\delta = 3.21$(q,2), 3.6(br,1 + $H_2O$). 4.32 (t,2), 7.23(d,2), 7.79(d,2), 7.92(s,1), 8.26(s,1), 8.54 (br,3) and 9.74(s,1) ppm.

Preparation 3

N-(4-Cyanophenyl)methanesulfonamide

Dissolve 50.3 g (0.426 mol) 4-aminobenzonitrile in 250 mL $CH_2Cl_2$ with 36 mL (0.445 mol) pyridine. Chill the solution with an ice/MeOH bath and add 34 mL (0.42 mol) methanesulfonyl chloride dropwise, maintaining the reaction temperature below 0° C. Stir the reaction mixture under $N_2$ for 20 h at ambient temperature. After this time, filter the reaction mixture and extract with 3×250 mL 1 N NaOH. Acidify the aqueous layer with concentrated HCl to pH=7. Filter the precipitate to provide the title compound.

NMR ($CDCl_3$): $\delta = 3.03$(s,3), 7.37(d,2), 7.58(d,2) and 10.1(s,1) ppm.

Preparation 4

N-(4-Aminomethylphenyl)methanesulfonamide hydrochloride

Saturate 450 mL methanol with ammonia gas and add 45 g (0.229 mol) N-(4-cyanophenyl)methanesulfonamide and 4 g Raney Nickel catalyst. Hydrogenate the mixture at 52 psi for 2 h. After this time, filter the catalyst and evaporate the solvents. The resultant oil is dissolved in methanolic HCl. Remove the solvents to provide the title compound.

NMR (DMSO-$d_6$): $\delta = 3.00$(s,3), 3.95(s,2), 7.24(d,2), 7.46(d,2) and 8.51(br s,4) ppm.

Preparation 5

N-(2-Aminoethyl)-4-(1H-imidazol-1-yl)benzamide hydrochloride

Reflux 150 mL (2.25 mol) ethylenediamine, and 21.0 9 (0.097 mol) 4-(1H-imidazol-1-yl)benzoic acid methyl ester for about 24 h. The excess ethylenediamine is removed in vacuo and the residue is triturated with $H_2O$, filtered, and the water evaporated. The residue is dissolved in ethanol and treated with excess HCl gas to provide the title compound.

NMR (DMSO-$d_6$): $\delta = 3.02$(t,2), 3.57(quar,2), 7.15(s,1), 7.81(d,2), 7.88(s,1), 8.11(d,2), 8.42(s,1), 8.99(t,1 ), 7.95–8.80(br s,3) ppm.

Preparation 6

N-(2-Aminoethyl)-4-(1H-imidazol-1-yl)benzamide

Dissolve N-(2-aminoethyl)-4-(1H-imidazol-1-yl)benzamide hydrochloride in 50 mL H$_2$O and pour onto a column of hydroxide anion exchange resin. Flush the column with H$_2$O and collect fractions with pH>8. Combine the basic fractions and remove the solvents in vacuo to obtain the free base.

Preparation 7

1 4-(4-Nitrophenyl)-1-(phenylmethyl)piperazine

Reflux a mixture of 53.5 mL (0.504 mol) of 1-fluoro-4-nitrobenzene, 99.14 g (0.555 mol) of 1-benzylpiperazine, and 76.7 g (0.555 mol) potassium carbonate in acetonitrile for about 17 h. Cool the mixture to room temperature and dilute with methylene chloride and filter. Concentrate the filtrate in vacuo. Dissolve the residue in methylene chloride and wash with water. Dry the organic layer with anhydrous sodium sulfate and concentrate in vacuo to give the title compound. NMR (DMSO-d$_6$): $\delta$=2.59(t,4),3.42(t,4), 3.57(s,2), 6.80(d,2) 7.34(m,5) and 8.11(d,2) ppm.

Preparation 8

4-[4-(Phenylmethyl)piperazin-1-yl]benzenamine

Add 474 g (2.10 mol) tin chloride dihydrate to a refluxing solution of 125 g (0.420 mol) 4-(4-nitrophenyl)-1-(phenylmethyl)piperazine in ethanol. Reflux the solution for about 15 h then cool to room temperature and remove the solvent. Dissolve the residue in water and adjust to pH 12 with sodium hydroxide. Extract the aqueous solution with methylene chloride and dry the organic layer with anhydrous sodium sulfate. Concentration at reduced pressure gives the title compound.

NMR (DMSO-d$_6$) $\delta$=2.61(t,4), 3.05(t,4), 3.41(br s,2), 3.56(s,2), 6.63(d,2), 6.81(d,2) and 7.25–7.36(m,5) ppm.

Preparation 9

N-[4-[4-(Phenylmethyl)piperazin-1-yl]phenyl]

methanesulfonamide 1.2 hydrochloride

To a chilled solution of 9.50 g (35.5 mmol) of 4-[4-(phenylmethyl)piperazin-1-yl]benzenamine in 100 mL of anhydride in 50 mL of acetonitrile. Allow the reaction mixture to stir at room temperature for 5 h. After this time, filter the resulting precipitate, add 100 mL of saturated aqueous sodium bicarbonate solution and extract this solution with 2×100 mL of methylene chloride. Wash the combined methylene chloride layers with 100 mL of saturated aqueous sodium chloride solution. Remove the solvent in vacuo. Dissolve the residue in 100 mL of methanol and acidify to pH=1 solution with hydrogen chloride gas. The solution is cooled and the resulting solid filtered to obtain the title compound.

NMR (DMSO-d$_6$): $\delta$=2.87(s,3), 3.03–3.25(m,4), 3.33 (d,2), 3.63–3.81(m,2), 4.37(d,2), 6.96(d,2), 7.12(d,2), 7.47(m,3), 7.66(m,2), 9.37(br s,1) and 11.38(br s,1) ppm.

Preparation 10

N-[4-(Piperazin-1-yl)phenyl]methanesulfonamide hydrochloride

Hydrogenolyze a suspension of 7.03 g (18.2 mmol) of N-[4-[4-(phenylmethyl)piperazin-1-yl]phenyl]methanesulfonamide in 400 mL of 50% aqueous ethanol over 0.35 g of 10% palladium on activated carbon catalyst at 50 psi. At the completion of the reaction remove the catalyst by filtration and evaporate the solvent in vacuo. Recrystallize the residue from ethanol to obtain the title compound.

NMR (D$_2$O): $\delta$=3.08(s,3), 3.48(m,B), 7.16(d,2) and 7.31(d,2) ppm.

Preparation 11

1-[4-[Methylsulfonyl)amino]benzoyl]-4(phenylmethyl)-piperazine hydrochloride To a cold solution of 29.8 g (0.169 mol) N-benzylpiperazine in 200 mL THF, slowly add a solution of 39.5 9 (0.169 mol) 4-[(methylsulfonyl)amino]benzoyl chloride in 200 mL THF, maintaining the reaction temperature below 0° C. When the addition is complete, stir the reaction at ambient temperature for 24 h. After this time, evaporate the solvents to give a dark oil. Dissolve the residue in 6 M NaOH (pH=14) and wash 3×200 mL ether. Acidify the aqueous layer with concentrated hydrochloric acid to pH=8. Collect the resulting solid via suction filtration to give the title compound as the free base. Dissolve the solid in methanol and acidify with HCl gas. Remove the solvents to give the HCl salt which can be recrystallized from 95% ethanol.

NMR (DMSO-d$_6$): $\delta$=3.06(s,3), 3.10–4.20(m,8), 4.33 (m,2), 7.25(d,2), 7.44(d,2), 7.46(br s,3), 7.59(br s,2), 10.13(s,1) and 11.10(br s,1) ppm.

Preparation 12

1-[4-[[(Methylsulfonyl)amino]benzoyl]piperazine hydrochloride

Dissolve 26.97 g (0.071 mol) 1-[4-[(methylsulfonyl)amino]benzoyl]-4-(phenylmethyl)piperazine hydrochloride in 500 mL water with 2.75 g 10% palladium on carbon. Hydrogenate at 52 psi in a Parr shaker for 18 h. After this time, filter the catalyst and remove the solvents to give the title compound which can be recrystallized from EtOH.

NMR (DMSO-d$_6$): $\delta$=3.06(s,3), 3.12(m,4), 3.71(m,4), 7.27(d,2), 7.44(d,2) and 9.82(br s,3) ppm.

Preparation 13

N-[2-[bis(Phenylmethyl)amino]ethyl]-propanamide

To a chilled solution of 5.0 g (21 mmol) N,N-dibenzylethylenediamine and 30 mL (21 mmol) triethylamine in 20 mL THF is added 1.8 mL (21 mmol) propionyl chloride, dropwise. The temperature of the reaction mixture is maintained below 0° C. during addition. The reaction mixture is stirred for 30 minutes at 0° C. After this time, the reaction mixture is filtered and the solvents are evaporated to give the product which can be purified via column chromatography.

NMR (CDCl$_3$): $\delta$=1.10(t,3), 2.12(quar,2), 2.58(t,2), 3.30(m,2), 3.60(s,4), 5.78(br s,1) and 7.30(m,10) ppm.

Preparation 14

N N-bis(Phenylmethyl)-N'-propyl-1 2-ethanediamine

To a chilled solution of 4.12 g (0.109 mol) lithium aluminum hydride in 200 mL THF is added a solution of 32.44 g (0.109 mol) N-[2-[bis(phenylmethyl)amino]ethyl]propanamide in 50 THF. The temperature during addition is maintained below 0° C. The reaction mixture is stirred at room temperature for 18 h, then is refluxed for 4 h. After this time, the reaction mixture is cooled and is quenched with H$_2$O. The quenched solution is stirred at room temperature for 18 h. After this time, the salts are removed by filtration and the solvents are evaporated to give the title compound.

NMR (CDCl₃): δ=0.86(t,3), 1.42(quint,2), 1.76 (br s,1), 2.36(t,2), 2.64(m,2), 4.60(s,4) and 7.30(m,10) ppm.

Preparation 15

N-[2-[[bis(Phenylmethyl)amino]ethyl]]-N-propyl-4-[(methylsulfonyl)amino]benzamide To a cold solution of 24.10 g (0.085 mol) N,N-bis-(phenylmethyl)-N'-propyl-1,2-ethanediamine in 250 mL THF with 12.5 mL (0.089 mol) triethylamine is added dropwise to a solution of 20.0 (0.085 mol) 4-[(methylsulfonyl)amino]benzoyl chloride in 50 mL THF. The temperature is maintained below 0° C. during addition. The reaction mixture is stirred at room temperature for 18 h. After this time, the solution is filtered and the solvents are evaporated to give the crude product which is purified via column chromatography on silica gel [petroleum ether : acetone, 9:1].

NMR (DMSO-d₆, 110° C.): δ=0.65(t,3), 1.38(quint,2), 2.62(t,2), 2.98(s,3), 3.12(t,2), 3.40(t,2), 3.58(s,4), 7.15(m,14) and 9.50(br s,1) ppm.

Preparation 16

N-[2-[(Phenylmethyl)amino]ethyl]-N-propyl-4-[(methylsulfonyl)amino]benzamide hydrochloride To a solution of 13.09 g (27.3 mmol) N-[2-[bis(phenylmethyl)amino]ethyl]-N-propyl-4-[(methylsulfonyl)amino]benzamide in 75 mL 80% aqueous methanol is added 27.3 mL 1 N HCl and 1.6 g 10% palladium on charcoal. The solution is hydrogenated at 50 psi for 75 minutes. After this time, the reaction mixture is diluted with 100 mL methanol, filtered and the solvents are evaporated to yield the title compound.

NMR (DMSO-d₆, 100° C.): δ=0.74(t,3), 1.51(quint,2), 3.01(s,3), 3.12(t,2), 3.26(t,2), 3.76(t,2), 4.15(s,2), 7.28(m,2), 7.39(m,5), 7.59(m,2) and 9.60(br s,2) ppm.

Preparation 17

N-[2-[[2-Hydroxy-3-phenyloxypropyl](phenylmethyl)amino]ethyl]-N-propyl-4-[(methylsulfonyl)amino]benzamide To a solution of 7.95 9 (20 mmol) N-[2-(phenylmethyl)amino)ethyl]-N-propyl-4-[(methylsulfonyl)amino]-benzamide in 20 mL 10% aqueous methanol is added 2.89 mL (21 mmol) 1,2-epoxy-3-phenoxypropane. The solution is stirred at room temperature for 24 h. After this time, the solvents are evaporated and the title compound is obtained as a foamy solid via column chromatography on silica gel (hexane:acetone, 9:1).

NMR (DMSO-d₆, 100° C.): δ=0.72(t,3), 1.43(quint,2), 2.49–2.63(m,2), 2.69(t,2), 2.96(s,3), 3.17(t,2), 3.38(t,2), 3.63(d,2), 3.81–3.92(m,3), 4.42(br s,1), 6.87(m,3), 7.21(m,11) and 9.56(br s,1) ppm.

Preparation 18

2-[4-(1H-Imidazol-1-yl)phenoxy]-N-(phenylmethyl)ethanamine dihydrochloride

To a suspension of 39.5 g (0.82 mol) sodium hydride in 500 mL DMF add 37.3 g (0.233 mol) 4-(1H-imidazol-yl)phenol portionwise. Chill the reaction mixture on an ice/MeOH bath during the addition. After addition, stir the reaction mixture at room temperature until gas evolution ceases. After this time, return the reaction mixture to the ice bath and add 50.2 g (0.29 g) N-benzyl-2-chloroethylamine hydrochloride portionwise. After addition is complete, heat the stirring suspension to 65° C. Follow the progress of the reaction by thin-layer chromatography on silica gel (methylene chloride:methanol, 9:1). At the completion of the reaction, cool to room temperature and slowly add 20 mL H₂O. Remove the solids by suction filtration and evaporate the solvents. Chromatograph the resulting oil on silica gel using (CH₂Cl₂:MeOH, 98:2), to isolate the title compound as the free base. Dissolve the free base in excess 3 M methanolic HCl and evaporate the solvents to give the title compound.

NMR (DMSO-d₆) δ=3.25(m,2), 3.42(br, 2 +H₂O), 4.25 (s,2), 4.44(t,2), 7.23(d,2), 7.43(m,3), 7.64(m,2), 7.78 (d,2), 7.91(m,1 ), 8.24(m,1), 9.70(s,1) and 10.0(m,1) ppm. 2HCl +H₂O at 3.35 ppm.

Preparation 19

1-[[2-[4-(1H-Imidazol-1-yl)phenoxy]ethyl](phenylmethyl)amino]-3-phenoxy-2-propanol To a solution of 3.2 mL (23.9 mmol) 1,2-epoxy-3-phenoxypropane in 20 mL MeOH, add 6.99 g (23.9 mmol) 2-[4-(1H-imidazol-1-yl)phenoxy]-N-(phenylmethyl)ethanamine as the free base described above. Stir at room temperature under a nitrogen atmosphere. Follow the progress of the reaction by thin-layer chromatography on silica gel (methylene chloride:methanol, 9:1). At the completion of the reaction, evaporate the solvents. The resulting oil is chromatographed on a silica gel column using (petroleum ether :acetone, 8:2). Collect the appropriate fractions and remove the solvents to give the title compound.

NMR (CDCl₃: δ=2.81–3.18(m,4), 3.85(br s,1), 3.74 (d,1), 3.90(d,1), 3.96–4.20(m,5), 6.86–6.97(m,6), 7.18–7.33(m,10) and 7.44(s,1) ppm.

Preparation 20

2-[[2-[4-(1H-Imidazol-1-yl)phenoxy]ethyl](phenylmethyl)amino]-1-(2-methoxyphenyl)ethanone Dissolve 5.06 g (17.2 mmol) 2-[4-(1H-imidazol-1-yl)phenoxy]-N-(phenylmethyl)ethanamine in 20 mL acetonitrile with 3.0 mL (17.2 mmol) ethyldiisopropylamine. Chill the solution in an ice/methanol bath and add 3.93 g (17.2 mmol) α-bromo-2-methoxyacetophenone dropwise. Allow the reaction to warm to room temperature and stir for 24 h. After this time, remove the solvents in vacuo. Chromatograph the residue on silica gel using 3% methanol in methylene chloride. Collect the appropriate fractions and remove the solvents to give the title compound.

NMR (DMSO-d₆): δ=3.00(t,2), 3.78(s,3), 3.84(s,2), 4.02(s,2), 4.10(t,2), 6.96–7.18(m,5), 7.32(m,5), 7.52(m,4), 7.66(s,1) and 8.14(s,1) ppm.

Preparation 21

N-[4-[2-[[2-[4-(1H-Imidazol-1-yl)phenoxy]ethyl](phenylmethyl)amino]-1-oxoethyl]phenyl]methanesulfonamide Add 5.87 g (16 mmol) 2-[4-(1H-imidazol-1-yl)phenoxy]-N-(phenylmethyl)ethanamine dihydrochloride to a solution of 1.8 g (32 mmol) potassium hydroxide in 50 mL water. Extract the solution with 3×100 mL CH₂Cl₂ and dry the organic layers with sodium sulfate. Evaporation of the solvents gives 2-[4-(1H-imidazol-1-yl)phenoxy]-N-(phenylmethyl)ethanamine as a pasty solid. Add the free base to a solution of 2.8 mL (16 mmol) ethyldiisopropylamine in 10 mL acetonitrile.

Chill the solution in an ice/methanol bath and add N-[4-(2-bromo-1-oxoethyl)phenyl]methanesulfonamide dropwise. Allow to warm to room temperature and stir for 18 h. After this time, remove the solvents in vacuo and dissolve the residue in 50 mL 6 N NaOH. Wash the basic solution 1×25 mL diethyl ether. Adjust the pH of the aqueous layer to pH=6 with concentrated HCl and extract with CH$_2$Cl$_2$. Dry the methylene chloride layers with anhydrous sodium sulfate and evaporate the solvents to give the title compound.

NMR (CDCl$_3$): δ=3.04(s,3), 3.12(t,2), 3.92(s,2), 4.04(s,2), 4.12(t,2), 6.78(d,2), 7.3(m,12), 7.84(s,1), 7.92(s,1) and 7.96(s,1) ppm.

Preparation 22

1-[[2-[4(1H-Imidazol-1-yl)phenoxy]ethyl](phenylmethyl)amino]-3-[4-(2-methoxyethyl)phenoxy]-2-propanol Combine 7.3 g (25 mmol) 2-[4-(1H-imidazol-1-yl)phenoxy]-N-(phenylmethyl)ethanamine dihydrochloride and 5.2 g (25 mmol) 1,2-epoxy-3-[4-(2-methoxyethyl)phenoxy]propane in 75 mL methanol and heat to 50° C. Follow the progress of the reaction by thin-layer chromatography on silica gel (acetonitrile:ammonia, 9:1). At the completion of the reaction, evaporate the solvents. Chromatograph the resulting oil on silica gel using 3% methanol in methylene chloride to give the title compound.

Preparation 23

1-[[2-[4-(1H-Imidazol-1-yl)phenoxy]ethyl](phenylmethyl)amino]-3-(3-methylphenoxy)-2-propanol To a solution of 2.75 g (17 mmol) 2,3-epoxypropyl 3-methylphenyl ether in 50 mL methanol add 4.4 g (15 mmol) 2-[4-(1H-imidazol-1-yl)phenoxy]-N-(phenylmethyl)ethanamine and heat to 50° C. for 24 h. Follow the progress of the reaction by thin-layer chromatography on silica gel (methylene chloride:methanol, 9:1). At the completion of the reaction, evaporate the solvents. The resulting oil is chromatographed on a silica gel column using 2% methanol in methylene chloride to provide the title compound.

NMR (CDCl$_3$): δ=2.31(s,3), 2.75–3.10(n,4) 3.80 (br, s,1), 3.75(d,1), 3.90(d,1), 3.94–4.10(m,5), 6.85–7.00 (m,6), 7.20–7.30(m,10) and 7.50(s,1) ppm.

Preparation 24

2-[4-(1H-Imidazol-1-yl)phenoxy]-1,1-dimethylethanamine dihydrochloride

Dissolve 27.0 g (0.106 mol) of N-[-2-[4-(1H-imidazol-1-yl)phenoxy]-1,1-dimethylethyl]acetamide in 270 mL of 2 N of hydrochloric acid and heat to reflux for 18 h. After this time, remove the water on the rotary evaporator and redissolve the residue in 50 mL of isopropanol. Remove the isopropanol on a rotary evaporator and suspend the resulting solid in diethyl ether. Filter off the solid to provide the title compound.

NMR (DMSO-d$_6$): δ=1.40(s,6), 3.6(br,1), 4.12(s,2), 7.24(d,2), 7.80(m,2), 7.92(m,1), 8.26(m,1), 8.60(br s,3) and 9.74(m,1) ppm.

Preparation 25

1-[4-(2-Methyl-2-propenyloxy)phenyl]-1H-imidazole

Suspend 40 g (0.25 mol) of 4-(1H-imidazol-1-yl)phenol in 280 mL of THF and treat with 15 9 (0.375 mol) of a 60% dispersion of sodium hydride in mineral oil. Stir this suspension for 20 min and then add 27.1 mL (0.25 mol) of 3-chloro-2-methylpropene. Heat this mixture to 100° C. for 3 h. After this time, add 250 mL of water and 250 mL of diethyl ether and separate the layers. Re-extract the aqueous layer with 2×250 mL of diethyl ether. Evaporate the combined ether extracts on a rotary evaporator. Triturate with 300 mL of hexanes and filter off the resulting solid to provide the title compound.

NMR (CDCl$_3$): δ=1.84(s,3), 4.48(s,2), 5.03(s,1), 5.11 (s,1), 7.00(d,2), 7.20(d,2), 7.30(m,2) and 7.76(s,1) ppm.

Preparation 26

N-[-2-[4-(1H-Imidazol-1-yl)phenoxy]-1,1-dimethylethyl]acetamide

Dissolve 27 g (0.126 mol) of 1-[4-(2-methyl-2-propenyloxy)phenyl]-1H-imidazole in a solution of 78 mL of glacial acetic acid and 29 mL of acetonitrile. Cool this solution to 0° C. over an ice bath and add 29.0 mL of 95% sulfuric acid dropwise at a rate to keep temperature below 15° C. Upon completion of the addition, stir overnight at room temperature. After this time, make basic (pH=12–14) with 4 N sodium hydroxide. Dilute with 400 mL of water and extract with 3×400 mL of diethyl ether. Concentrate the combined ether extracts to 350 mL on the rotary evaporator and cool in the refrigerator for 1 h. Filter off the resulting precipitate to provide the title compound.

NMR (DMSO-d$_6$): δ=1.33(s,6), 1.78(s,3), 4.10(s,2), 7.04(d,2) 7.07(s,1), 7.54(d,2), 7.62(s,1), 7.64(s,1) and 8.13(s,1) ppm.

Preparation 27

2-[4-(1H-Imidazol-1-yl)phenoxy]-1,1-dimethylethanamine

Partially dissolve 30.69 g (0.1 mol) of 2-[4-(1H-imidazol-1-yl)phenoxy]-1,1-dimethylethanamine dihydrochloride in 50 mL of water and make basic with 70 mL 4 N NaOH. Extract this mixture with 2×100 mL of methylene chloride. Remove the solvent on a rotary evaporator to provide the title compound.

NMR (CDCl$_3$): δ=1.22(s,6), 1.59(br s,2), 3.71(s,2), 7.00(d,2), 7.18(s,1), 7.20(s,1), 7.27(d,2) and 7.77(s,1) ppm.

EXAMPLES

Example I

N-[4-[[2-Hydroxy-3-(3-methylphenoxy)propyl]aminomethyl]phenyl]methanesulfonamide hydrochloride Heat a mixture of N-[4-(aminomethyl)phenyl]methanesulfonamide hydrochloride (15.0 g, 63.4 mmol) and 1,2-epoxy-3-phenoxypropane (10.41 g, 63.4 mmol) in 63.4 mL of 1 N KOH in methanol and 10 mL of water for about 3.5 h. Remove the solvent to afford crystals of the title compound.

NMR (DMSO-d$_6$): δ=2.27(s,3), 2.85–3.15(m,2), 3.02 (s,3), 3.93(s,2), 4.14(s,2), 4.23(br s,1), 5.90(br s,1), 6.74(m,3), 7.19(m,1), 7.24(d,2), 7.53(d,2), ca. 9.35 (br s,2) and 9.97(s,1) ppm.

Example II

N-[4-[[2-Hydroxy-3-[4-(2-methoxyethyl)phenoxy]-propyl]aminomethyl]phenyl]methanesulfonamide hydrochloride 1,2-epoxy-3-[4-(2-methoxyethyl)phenoxy]propane (63.7 mmol) in 15 mL of MeOH is added dropwise to a solution of N-[4-(aminomethyl)phenyl]methanesulfonamide hydrochloride (62.4 mmol) in 1M KOH in MeOH (65 mL) at room temperature. $H_2O$ (5 mL) is added ad the mixture is refluxed overnight. Methanol is removed from the cooled mixture under reduced pressure, and the residue is partitioned between $H_2O$ and $CH_2Cl_2$, and the combined organic portions are washed with brine and dried with anhydrous $Na_2SO_4$. After removal of the solvent under reduced pressure the hydrochloride salt is formed and recrystallized with $CH_3CN$/MeOH to yield the title compound.

Example III

N-[4-[(2-Hydroxy-3-phenoxypropyl)aminomethyl]-phenyl]methanesulfonamide hydrochloride To a solution of 18.0 g (0.76 mmol) of N-[4-(aminomethyl)phenyl]methanesulfonamide hydrochloride in 200 mL of methanol, add a solution of 3.04 g of sodium hydroxide in 10 mL of water. Stir for fifteen minutes. Add 11.14 g (0.076 mmol) of 1,2-epoxy-3-phenoxy propane and reflux for 4.5 h. Monitor the progress of the reaction by thin-layer chromatography on silica gel (acetonitrile:ammonium hydroxide, 9:1). Remove the solvent in vacuo. Chromatograph the oil on 800 g of silica gel using a mixture of methylene chloride:methanol:triethylamine (97:2:1) initially and changing to methylene chloride, methanol, triethylamine (95:4:1). Combine the fractions containing product and remove the solvent in vacuo. Dissolve the product in methanol and add a solution of hydrogen chloride in methanol. Remove the solvent in vacuo. Recrystallize the salt from acetonitrile:methanol to obtain the title compound.

NMR (DMSO-$d_6$): $\delta = 2.94(t,1)$, 3.08(s,3), 3.12(m,1), 4.01(d,2), 4.20(s,2), 4.23(m,1), 5.88(d,1), 6.94(m,3), 7.27(m,4), 7.52(d,2), 9.97(br s,2) and 10.10(br s,1) ppm.

Example IV

N-[2-[[2-Hydroxy-3-(4-methoxyphenoxy)propyl]amino]ethyl]-4-(1H-imidazol-1-yl)benzamide To a solution of 2.39 g (13.2 mmol) 1,2-epoxy-3-(4-methoxyphenoxy)propane in 25 mL methanol is added 3.05 g (13.2 g) N-(2-aminoethyl)-4-(1H-imidazol-1-yl)benzamide. The reaction mixture is stirred under a nitrogen atmosphere for 24 h. After this time, the precipitate is collected and recrystallized from ethanol to provide the title compound.

NMR (DMSO-$d_6$, 60° C.): $\delta = 2.58-2.75(m,2)$, 2.75(t,2), 3.15(br sl, +$H_2O$), 3.37(quar,2), 3.67(s,3), 3.80-3.98 (m,3), 4.72(br, s,1), 6.83(m,4), 7.12(s,1), 7.72(d,2), 7.77 (s,1), 7.97(d,2), 8.29(s,1) and 8.32(br s,1) ppm.

Example V

N-[2-[[2-Hydroxy-3-(1-naphthalenyloxy)propyl]amino]ethyl]-4-(1H-imidazol-1-yl)benzamide (Z)-butenedioic acid salt (1:1)

To a solution of 34.45 g (0.172 mol) 1,2-epoxy-3-(1-naphthalenyloxy)propane in 275 mL methanol add 39.62 g (0.172 mol) N-(2-aminoethyl)-4-(1H-imidazol-1-yl)benzamide. Stir the reaction mixture under a nitrogen atmosphere for 24 h. After this time, remove the solvents in vacuo to obtain an oil. Chromatograph the oil on a silica gel column using acetonitrile then acetonitrile:methanol, 4:1 as eluent. Combine the appropriate fractions and remove the solvents. Dissolve the residue in hot ethanol with one equivalent of maleic acid. Chill the solution and filter the solid to give the title compound.

NMR (DMSO-$d_6$): $\delta = 3.08-3.52(m,6)$, 3.52-3.76(m,2), 4.08-4.24(m,2), 4.08-4.46(br s,1), 6.03(s,3), 6.98(d,2), 7.15(s,1), 7.40-7.62(m,4), 7.76-7.96(m,3 maleic acid), 8.02(d,2), 8.27(d,2), 8.41(s,1), 8.66(br s,1) and 8.78(t,1) ppm.

Example VI

N-[2-[[2-Hydroxy-3-(4-(2-methoxyethyl)phenoxy)-propyl]amino]ethyl]-4-(1H-imidazol-1-yl)benzamide To a solution of 10 g (37.5 mmol) N-(2-aminoethyl)-4-(1H-imidazol-1-yl)benzamide hydrochloride in 50 mL methanol and 5 mL water with 1.69 g (42 mmol) sodium hydroxide, add 8.59 g (41.2 mmol) 1,2-epoxy-3-[4-(2-methoxyethyl)phenyl]propane. Heat the mixture to 60° C. for about 18 h. Cool the reaction mixture to room temperature and remove the solvents in vacuo. The resulting oil is chromatographed on alumina (activity III) using $CH_2Cl_2$:MeOH, 98:2. Combine the appropriate fractions and remove the solvents to give the title compound which can be recrystallized from ethyl acetate.

NMR ($CDCl_3$): $\delta = 2.85(t,2)$, 2.90(m,2), 2.95(t,2), 3.78 (s,3), 3.59(t,2), 3.62(m,2), 4.00(m,2), 4.15(m,1), 6.85(d,3), 7.16(d,2), 7.28(d,2), 7.29(s,1), 7.35(s,1), 7.45 (d,2) and 7.93(d,3) ppm.

Example VII

N-[4-[4-(2-Hydroxy-3-phenoxypropyl)piperazin-1-yl]phenyl]methanesulfonamide

Suspend a mixture of 20.0 g (56.9 mmol) of N-[4-(piperazin-1-yl)phenyl]methanesulfonamide methanesulfonate, 7.68 mL (56.9 mmol) of 1,2-epoxy-3-phenoxypropane and 3.07 g (56.9 mmol) of sodium methoxide in 800 mL of 90% aqueous methanol and warm to 60° C. for 18 h. After 18 h, filter the precipitate and wash this precipitate with 100 mL of water and 100 mL of methanol. Suspend this solid precipitate in 500 mL of methanol and reflux for 1 h. After 1 h, cool the suspension to room temperature and filter to obtain the title compound.

NMR (DMSO-$d_6$): $\delta = 2.57(dd,2)$, 2.6(m,4), 2.85(s,3), 3.0(br s,1), 3.12(t,4), 3.93(m,1), 3.97(m,2), 6.88(m,3), 6.94(d,2), 7.09(d,2), 7.25(m,2) and 8.9(br s,1) ppm.

Example VIII

N-[4-[4-[3-[[[bis(Cyclopropyl)methyl]imino]oxy]-2-hydroxypropyl]piperazin-1-yl]phenyl]methanesulfonamide N-[4-(Piperazin-1-yl)phenyl]methanesulfonamide (25 mmol) in 50 mL of 9:1, MeOH:$H_2O$ is heated to 50° C. A solution of dicyclopropylmethanone-0-(oxiranylmethyl)oxime (28 mmol) in 50 mL of 9:1 MeOH:$H_2O$ is added to the hot solution and heated at reflux for two days. The solvent is removed from the reaction mixture under reduced pressure, and the residue is partitioned between $CH_2Cl_2$ and $H_2O$. The aqueous portion is extracted with $CH_2Cl_2$, and the combined organic portion are washed with brine and dried with $Na_2SO_4$. Removal of the solvent under reduced pressure yields the product which is recrystallized from ethyl acetate.

NMR (DMSO-$d_6$):δ=0.46-0.60(m,4), 0.78-0.86(m,2), 0.86-0.95(m,2), 0.95-1.08(m,1), 2.25-2.45(m,3), 2.52-2.60 (m,4 +DMSO), 2.85(s,3), 3.02-3.10(m,4), 3.80-3.90(m,3), 4.59-4.61(m,1), 6.88(d,2), 7.08(d,2) and 9.22(br s,1) ppm. Ethyl acetate present at 1.18, 2.00 and 4.01 ppm.

Example IX

N-[4-[4-[2-Hydroxy-3-(3-methylphenoxy)propyl]piperazin-1-yl]phenyl]methanesulfonamide dihydrochloride Heat a mixture of 5.0 g (19.6 mmol) N-[4-(piperazin-1-yl)phenyl]methanesulfonamide and 3.22 g (19.6 mmol) 1,2-epoxy-3-(3-methylphenoxy)propane in 50 mL of methanol and 2 mL of water at reflux for about 8 h. Cool the reaction to room temperature and collect the precipitate. Dissolve the solid in ethanol and bubble hydrochloric acid gas through the solution until the pH is 2.0. Concentrate the solution in vacuo to give the title compound.

NMR (DMSO-$d_6$): δ=2.29(s,3), 2.89(s,3), 3.09-3.39(m,6), 3.60-3.80(m,4), 3.94-4.01(m,2), 4.42(m,1), ca. 5.25(br s,2), 6.75-6.79(m,3), 7.00(d,2), 7.12-7.21(m,3), 9.37(s,1) and 10.27(br s,1) ppm.

Example X

N-[4-[4-[2-Hydroxy-3-(2-methylphenoxy)propyl]piperazin-1-yl]phenyl]methanesulfonamide hydrochloride Heat a mixture of 5.0 g (19 mmol) N-[4-(-piperazin-1-yl)phenyl]methanesulfonamide and 3.5 g (21.3 mmol) 1,2-epoxy-3-(2-methylphenoxy)propane in 50 mL MeOH and 5 mL water. Reflux for 6 h. After this time, allow the reaction mixture to cool to room temperature and filter the resulting precipitate. Dissolve the precipitate in excess methanolic HCl and concentrate in vacuo to provide the title compound which can be recrystallized from ethanol.

NMR (DMSO-$d_6$): δ=2.20(s,3), 2.88(s,3), 3.29(m,7), 3.85(m,3), 3.97(t,2), 4.22(br s,1), 6.0(s,1), 6.86-7.00(m,4), 7.13(m,4), 9.37(s,1) and 10.2(br s,1) ppm.

Example XI

N-[4-[4-[2-Hydroxy-3-(5,6,7,8-tetrahydro-5-oxo-1-naphthalenyloxy)propyl]-1-piperazinyl]phenyl]methanesulfonamide dihydrochloride Heat a mixture of 5.5 g (21.6 mmol) N-[4-piperazin-1-yl)phenyl]methanesulfonamide and 4.7 g (21.6 mmol) 1,2-epoxy-3-(5,6,7,8-tetrahydro-5-oxo-1-naphthalenyloxy)propane in 75 mL methanol and 5 mL water at 60° C. for about 17 h. Cool the reaction mixture and remove the solvents to give an off white solid. Suspend the solid in 100 mL methanol and acidify with 4 mL of 12 M hydrochloric acid. Remove the solvents to give a white solid which is recrystallized from ethanol to give the title compound.

NMR (DMSO-$d_6$): δ=2.04(m,2), 2.59(t,2), 2.89(s,3), 2.90(m,2), 3.14-3.43(m,6), 3.63-3.79(m,4), 4.04(m,2), 4.49 (br s,1), 5.25(br s,2 +$H_2O$), 7.00(d,2), 7.13(d,2), 7.26 (d,2), 7.32(t,1), 7.50(d,1), 9.38(s,1) and 10.50(br s,1)

Example XII

N-[4-[4-[2-Hydroxy-3-[4-(2-methoxyethyl)phenoxy]propyl]piperazin-1-yl]phenyl]methanesulfonamide dihydrochloride Heat a mixture of 5.0 g (19.6 mmol) N-[4-(piperazin-1-yl)phenyl]methanesulfonamide and 4.08 g (19.6 mmol) 1,2-epoxy-3-[4-(2-methoxyethyl)phenoxy]propane in 75 mL of methanol and 5 mL of water at 60° C. for about 17 h. Cool the reaction to room temperature and collect the precipitate. Dissolve the solid in ethanol and bubble hydrochloric acid gas through the solution until the pH is 2.0. Concentrate the solution in vacuo to give the title compound.

NMR (DMSO-$d_6$): δ=2.74(t,2), 2.88(s,3), 3.10-3.50 (m,8), 3.23(s,3), 3.48(t,2), 3.66(t,2), 3.76(t,2), 3.95(m,2), 4.45(m,1), 6.88(d,2), 6.99(d,2), 7.13(d,2), 7.16(d,2), 9.37(s,1) and 10.32(br s,1) ppm.

Example XIII

4-[2-Hydroxy-3-[4-[4-[(methylsulfonyl)amino]phenyl]piperazin-1-yl]propoxy]benzeneacetamide hydrochloride Heat a mixture of 5.0 g (19.6 mmol) N-[4-(piperazin-1-yl)phenyl]methanesulfonamide and 4.06 g (19.6 mmol) 4-(oxiranylmethoxy)benzeneacetamide in 50 mL of methanol and 50 mL of water at 65° C. for about 28 h. Cool the reaction to room temperature and collect the precipitate. Dissolve the solid in hot methanol and bubble hydrochloric acid gas through the solution until the PH is 2.0. Concentrate the solution in vacuo to give the title compound.

NMR (DMSO-$d_6$): δ=2.88(s,3), 3.11-3.35(m,B), 3.60-3.75(m,4), 3.94(m,2), 4.46(br s,1), 6.01 (br s,1), 6.83(s,1), 6.90(d,2), 6.99(d,2), 7.13(d,2), 7.19(d,2), 7.44(s,1), 9.38(s,1) and 10.46(br s,1) ppm.

Example XIV

1-[2-Hydroxy-3-(1-naphthalenyloxy)propyl]-4-[4-[(methylsulfonyl)amino]benzoyl]piperazine Add 7.89 g (42.4 mmol) of 1,2-epoxy-3-(1-naphthalenyloxy)propane to a solution of 12.0 9 (42.4 mmol) of 1-[4-[(methylsulfonyl)amino]benzoyl]piperazine in methanol. Heat the resultant solution at reflux for about 46 h. Cool the solution to room temperature and evaporate the solvent. Triturate the residue with ether to obtain crystals of the title compound.

NMR (DMSO-$d_6$) δ=2.40-2.70(m,6), 3.04(s,3), 3.28-3.76(m,4), 4.04-4.22(m,3), 5.04(d,1), 6.95(d,1), 7.23 (d,2), 7.37(d,2), 7.39-7.57(m,4), 7.86(dd,1), 8.24(dd,1) and 10.03 (s,1) ppm.

Example XV

1-[2-Hydroxy-3-phenoxypropyl]-4-[4-[(methylsulfonyl)amino]benzoyl]piperazine phosphoric acid salt (1:1)

To a solution of 13.31 g (47 mmol) 1-[4-[(methylsulfonyl)amino]benzoyl]piperazine in 50 mL methanol add 6.4 mL (47 mmol) 1,2-epoxy-3-phenoxypropane. Stir the reaction mixture at room temperature under a nitrogen atmosphere. Follow the progress of the reaction by thin-layer chromatography on silica gel (methylene chloride: MeOH, 9:1). When the reaction is complete, remove the solvents in vacuo to obtain an oil. Dissolve the oil in ethanol with one equivalent of $H_3PO_4$ and remove the solvents to obtain the title compound.

NMR (DMSO-d$_6$): δ=2.53–2.65(m,6), 3.05(s,3), 3.52 (br s,4), 3.87–4.02(m,4), 6.93(m,3), 7.26(m,4), 7.38(d,2), 8.5(b 3) 10.05(b 1) ppm.

Example XVI

1-[2-Hydroxy-3-[4-(2-methoxyethyl)phenoxy]propyl]-4-[4-[(methylsulfonyl)amino]benzoyl] piperazine phosphoric acid salt (1:1)

Add 2.64 g (.013 mol) of 1,2-epoxy-3-[4-(2-methoxyethyl)phenoxy]propane to a solution of 3.86 (12 mmol) 1-[4-[(methylsulfonyl)amino]benzoyl]piperazine hydrochloride in 50 mL MeOH and 13 mL 1 N NaOH. Heat the resultant solution at 50° C. for about 24 h. Cool the solution to room temperature and evaporate the solvents. Dissolve the resultant oil in ethanol and acidify with one equivalent of phosphoric acid. Remove the solvents to obtain the title compound.

Example XVII

1-[[2-[4-(1H-Imidazol-1-yl)phenoxy]ethyl]amino]-3-phenoxy-2-propanol

To a solution of 5.5 g (12.4 mmol) 1-[[2-[4-(1H-imidazol-1-yl)phenoxy]ethyl](phenylmethyl)amino]-3-phenoxy-2-propanol in 25 mL methanol is suspended 1.0 g 10% palladium on carbon. The reaction mixture is hydrogenated at 50 psi in a Parr Hydrogenator. Follow the progress of the reaction by thin-layer chromatography on silica gel (methylene chloride:methanol, 9:1). At the completion of the reaction, the catalyst is filtered and the solvents are removed in vacuo. The isolated oil is taken up in methylene chloride, dried over anhydrous Na$_2$SO$_4$, filtered and the solvents are removed to give the title compound.

NMR (CDCl$_3$): δ=1.24(br s,2), 2.93(m,2), 3.10(t,2), 4.00(d,2), 4.13(t,3), 6.89–6.99(m,5), 7.18(m,2), 7.27 (m,4), and 7.75(s,1) ppm.

Example XVIII

α-[[[2-[4-(1H-Imidazol-1-yl)phenoxy]ethyl]amino]methyl]-2-methoxybenzenemethanol Dissolve 3.8 9 2-[[2-[4-(1H-imidazol-1-yl)phenoxy]ethyl](phenylmethyl)amino]-1-(2-methoxyphenyl)ethanone in 50 mL 5 M HCl in methanol and remove the solvents in vacuo. Dissolve the residue in 50 mL H$_2$O with 0.85 9 10% palladium hydroxide on charcoal. Hydrogenate the solution under 52 psi hydrogen for 20 h. After this time, filter the catalyst and remove the solvents to give the crude product. Recrystallize the solid from ethanol to give the title compound.

NMR (DMSO +D$_2$O, 100° C.): δ=3.09(m,1), 3.47(t,2), 3.82(s,3), 4.41(t,2), 2.27(m,1), 7.01(d,2), 7.18(d,2), 7.30(m,1), 7.47(d,1), 7.56(s,1), 7.66(d,2), 7.89(s,1), and 8.09(s,1) ppm.

Example XIX

N-[4-[1-Hydroxy-2-[[2-[4-(1H-imidazol-1-yl)phenoxy]ethyl]amino]ethyl]phenyl]methanesulfonamide Dissolve 4.0 g (0.7 mmol) of Preparation 21 in excess 4.0 M methanolic HCl and remove the solvents in vacuo. Dissolve the residue in 30 mL H$_2$O with 0.6 g palladium hydroxide on carbon. Hydrogenate the aqueous solution under 52 psi hydrogen gas. Follow the progress of the reaction by thin-layer chromatography (silica gel: acetonitrile:ammonia, 9:1); visualize via UV and iodoplatmate. When the reaction is complete, filter the catalyst and remove the solvents in vacuo. Recrystallize the residue from ethanol to obtain the title compound.

NMR (DMSO-d$_6$): δ=2.98(s,3), 3.21(m,2), 3.44(t,2), 4.42(t,2), 5.03(d,1), 6.24(br s,1), 7.23(d,4), 7.37(d,2), 7.76(d,2), 7.87(s,1), 8.21(s,1), 9.12(br s,1), 9.50(br s,1), 9.60(s,1) and 9.84(s,1) ppm.

Example XX

1-[[2-[4-(1H-Imidazol-1-yl)phenoxy]ethyl]amino]-3-[4-(2-methoxyethyl)phenoxy]-2-propanol Dissolve 6.36 g (.013 mol) 1-[[2-[4-(1H-imidazol-1-yl)phenoxy]ethyl](phenylmethyl)amino]-3-[4-(2-methoxyethyl)phenoxy]-2-propanol in 50 mL 5 M methanolic HCl and remove the solvents in vacuo. Dissolve the residue in glacial acetic acid with 0.86 g 10% palladium hydroxide on carbon. The reaction mixture is hydrogenated under 52 psi H$_2$ on a Parr Hydrogenator. Follow the progress of the reaction by thin-layer chromatography on silica gel (acetonitrile:ammonia, 9:1). At the completion of the reaction, the catalyst is filtered and the solvents are removed in vacuo. The resulting oil is chromatographed on alumina (activity III) using 2% methanol in methylene chloride to provide the title compound.

NMR (CDCl$_3$): δ=2.8–3.4(br s,2), 2.89(t,2), 2.90–3.10(m,2), 3.200t,2), 3.42(s,3), 3.63(t,2), 4.06(d,2), 4.25(m,3), 6.92(d,2), 7.05(d,2), 7.19(d,2), 7.25(m,2), 7.35(d,2) and 7.85(s,1) ppm.

Example XXI

1-[[2-[4-(1H-Imidazol-1-yl)phenoxy]ethyl]amino]-3-(3-methyl-phenoxy)-2-propanol phosphoric acid salt (1:1)

Dissolve 4.1 g (8.9 mmol) 1-[[2-[4-(1H-imidazol-1-yl)phenoxy]ethyl](phenylmethyl)amino]-3-(3-methyl-phenoxy)-2-propanol in 25 mL 4 M methanolic HCl and remove the solvents on a rotary evaporator. Dissolve the resulting oil in 40 mL glacial acetic acid and add 0.5 g 10% palladium hydroxide on carbon. The reaction mixture is hydrogenated at 50 psi H$_2$ in a Parr Hydrogenator. Follow the progress of the reaction by thin-layer chromatography on silica gel (methylene chloride:methanol, 9:1). At the completion of the reaction, the catalyst is filtered and the solvents are removed in vacuo. Chromatograph the resulting oil on silica using 2% methanol in methylene chloride to give the title compound as a free base. Dissolve the free base in 50 mL ethanol with 1 equivalent phosporic acid and remove the solvents on the rotary evaporator to give the title compound.

NMR (DMSO-d$_6$): δ=2.31(s,3), 2.95(dd,2), 3.17(t,2), 3.99(d,2), 4.05(m,1), 4.24(t,2), 6.33(br s, ca. 5), 7.09 (m,3), 7.13(m,4), 7.53(m,3) and 8.04(s,1) ppm. Trace ethanol at 1.05 ppm.

Example XXII

4-[2-Hydroxy-3-[[2-[4-(1H-imidazol-1-yl)phenoxy]-1,1-dimethylethyl]amino]-propyl]benzeneacetamide dihydrochloride Dissolve 7.0 g (30.1 mmol) of 2-[4-(1H-imidazol-1-yl)phenoxy]-1,1-dimethylethanamine and 7.64 g (39.2 mmol) of 4-(oxiranylmethoxy)benzeneacetamide in 100 mL of 90% aq. DMSO and heat to 115° C. for 18 h. After this time, add 100 mL water and extract with 3×100 mL of methylene chloride: methanol, 90:10. Combine the organic extracts and wash with 100 mL of water. Remove the solvent on the rotary evaporator and purify the residue by flash chromatography using flash silica gel (Baker) and eluting with acetonitrile:ammonia (aq.), 93:7. Combine the pure fractions and remove the solvent on the rotary evaporator. Dissolve this residue in 100 mL of isopropanol and remove the solvent on the rotary evaporator. Dissolve this residue in isopropanol and add 1.2 N methanolic hydrochloric acid to pH=1. Crystallize by cooling in the freezer for 24 h to provide the title compound.

NMR (DMSO-$d_6$): $\delta$=1.46(s,6), 2.9–4.2(br,1+$N_2$O), 2.98–3.4(m,2), 3.29(s,2), 3.99(m,2), 4.24(m,3), 5.96 (br s,1), 6.83(br s,1), 6.85(d,2), 7.16(d,2), 7.25(d,2), 7.48(br s,1), 7.78(d,2), 7.89(s,1), 8.23(s,1), 8.96 (br t,1), 9.5(br, t,1) and 9.68(s,1)ppm.

Example XXIII

1-[[[4-(1H-Imidazol-1-yl)phenyl]methyl]amino]-3-(2-methylphenoxy)-2-propanol dihydrochloride Dissolve 1.74 g (10.04 mmol) of 4-(1H-imidazol-1-yl)-benzenemethanamine in 20 mL of dry DMSO under nitrogen. Add 2.44 mL (11.55 mmol) of hexamethyldisilazane and stir at room temperature for 30 min. After this time, add a solution of 1.73 g (10.54 mmol) of 1,2-epoxy-3-(2-methylphenoxy)propane in 10 mL of DMSO and heat in an oil bath at 60° C. for 42 h. Follow the progress of the reaction by thin-layer chromatography on silica gel (acetonitrile: ammonia (aq), 90:10). At the completion of the reaction, add 6 N hydrochloric acid to pH=1 and then add 4 N sodium hydroxide to pH=12. Dilute this basic mixture with 20 mL of water and extract with 3×75 mL of methylene chloride. Remove the solvent on the rotary evaporator. Purify this residue by flash chromatography using flash silica gel (Baker) and eluting with a solution of acetonitrile: ammonia hydroxide 98:2. Combine pure fractions and remove the solvent on the rotary evaporator. Dissolve this residue in 50 mL of acetonitrile and remove the solvent on the rotary evaporator. Dissolve this residue in 10 mL of methanol and bubble hydrogen chloride through the solution until pH=1 is reached. Remove the solvent on the rotary evaporator and recrystallize the solid from 20 mL of isopropanol to provide the title compound.

NMR (DMSO-$d_6$): $\delta$=2.11(s,3), 3.0(m,1), 3.5(br s,2+$H_2$O), 3.97(m,2), 4.32(m,3), 6.66(t,1), 6.72(d,1), 7.13(m,2), 7.90(s,4), 7.93(s,1), 8.33(s,1), 9.5(br s,1), 9.78(s,1) and 9.88(br s,1) ppm.

Example XXIV

N-[4-[2-Hydroxy-3-[[2-[4-(1H-imidazol-1-yl)phenoxy]-1,1-dimethylethyl]amino]propoxy]phenyl]methanesulfonamide dihydrochloride Dissolve 6.21 g (26.7 mmol) of 2-[4-(1H-imidazol-1-yl)phenoxy]-1,1-dimethylethanamine and 6.62 g (27.21 mmol) of N-[4-(oxiranylmethoxy)phenyl]methanesulfonamide in 70 mL of 25% aq. DMSO and heat to 115° C. for 48 h. After this time, add 200 mL of water and 20 mL 2 N NaOH. Neutralize the aqueous layer to pH=8.5 with 1 N hydrochloric acid and extract into 3×300 mL of methylene chloride:methanol, 90:10. Wash the combined organic extracts with 100 mL of water and remove the solvent on the rotary evaporator. Purify this residue by flash chromatography using flash silica gel (Baker) and eluting with an acetonitrile: ammonia (aq.) gradient (98:2→95:5). Combine the pure fractions and remove the solvent on the rotary evaporator. Dissolve the resulting residue in 50 mL of isopropanol and then remove the solvent on the rotary evaporator. Dissolve this residue in methanol and acidify to pH 1 with 2 N methanolic hydrochloric acid. Remove the solvent on the rotary evaporator to provide a foamy residue. Stir this residue in 50 mL of diethyl ether for 2 h and filter to provide the title compound.

NMR (DMSO-$d_6$): $\delta$=1.46(s,6), 2.88(s,3), 2.92–3.45 (m,2), 3 45(br,1+$H_2$O), 3.99(m,2), 4.22(m,3), 6.0(br s,1), 6.92(d,2), 7.15(d,2), 7.26(d,2), 7.78(d,2), 7.90(s,1), 8.23(s,1), 8.9(br t,I), 9.46(m,1), 9.47(s,1) and 9.66(s,1) ppm.

Example XXV

Dicyclopropylmethanone-0-[2-hydroxy-3-[[2-[4-(1H-imidazol-1-yl)-phenoxy]ethyl]amino]propyl]oxime sulfuric acid salt (1:1)

To 60 mL of methanol under nitrogen atmosphere add 3.14 9 (17.3 mmol) of dicyclopropylmethanone-0-(oxiranylmethyl)oxime, 4.58 g (16.7 mmol) of 2-[4-(1H-imidazol-1-yl)phenoxy]ethanamine dihydrochloride and 20 mL of 2 N NaOH. Stir the mixture at 62° C. Monitor the progress of the reaction by thin-layer chromatography on silica gel $CH_2Cl_2$:MeOH, 9:1). Upon completion of the reaction remove the solvent in vacuo, add water, and extract with methylene chloride. Dry the organic layer over anhydrous $Na_2SO_4$. Remove the drying agent by filtration and remove solvent in vacuo. Chromatograph the resulting oil on 90 g of silica gel with $CH_2Cl_2$:MeOH, 9:1. Dissolve the resulting oil in methanol and add an equivalent of concentrated $H_2SO_4$. The solid material is removed by suction filtration to afford the title compound.

NMR (DMSO-$d_6$): $\delta$=0.59(m,4), 0.8–1.1(m,5), 2.30 (m,1), 2.98(m,1), 3.20(d,1), 3.42(br t,2), 3.88(dd,1), 3.97(dd,1), 4.10(br s,1), 4.34(br t,2), 5.88(br s,1), 7.10(s,1), 7.11(d,2), 7.60(d,2), 7.66(s,1), 8.15(s,1), 8.9(br,3).

Example XXVI

N-[4-[2-Hydroxy-3-[[2-[4-(1H-imidazol-1-yl)phenoxy]ethyl]amino]propoxy]phenyl]methanesulfonamide hydrochloride To a solution of 2.3 g (0.008 mol) of 2-[4-(1H-imidazol-1-yl)phenoxy]ethanamine dihydrochloride in 100 ml of methanol add a solution of 0.66 g of sodium hydroxide in 5 mL of water. Stir for 15 minutes. Add 2.0 g (0.008 mol) of N-[4-(oxiranylmethoxy)phenyl]methanesulfonamide and reflux for 16 h. Monitor the progress of the reaction by thin-layer chromatography on silica gel (methylene chloride, methanol, triethylamine, 84:15:1). Remove the solvent in vacuo. Chromatograph the oil on 350 g of silica gel using a mixture of methylene chloride:methanol:triethylamine (94:5:1). Combine the fractions containing residue and remove the solvent in vacuo. Dissolve the residue in methanol and add a solution of hydrogen chloride in methanol. Remove the solvent in vacuo. Recrystallize the salt from acetonitrile:methanol to obtain the title compound.

NMR (DMSO-$d_6$): $\delta$=2.88(s,3), 3.1(m,1), 3.25–3.40 (m,1), 3.42(m,2), 3.95(d,2), 4.20(br m,1), 4.31(t,2), 5.88(m,1), 6.95(d,2), 7.09(s,1), 7.12(d,2), 7.17(d,2), 7.60(d,2), 7.67(s,1), 8 16(s,1), ca. 8.8(br,2) and 9.42(s,1).

We claim:

1.

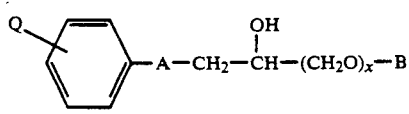

wherein:
Q is $(C_1-C_4)-SO_2NH-$ or

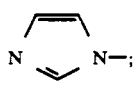

x is the integer 0 or 1;
A is

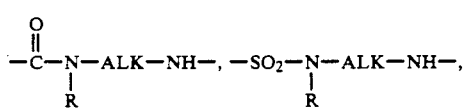

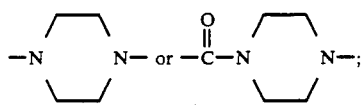

B is

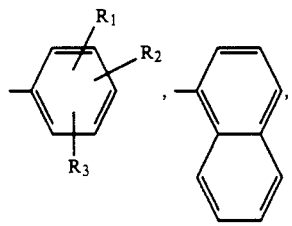

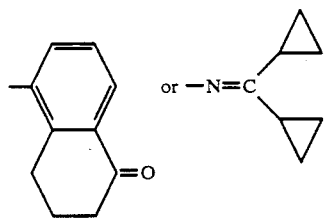

ALK is

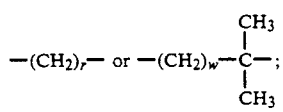

R is hydrogen, lower alkyl, 2-propenyl, lower alkoxylower alkyl;
$R_1$, $R_2$, $R_3$ are the same or different and selected from hydrogen, lower alkyl, lower alkoxy, 2-propenyl, 2-propenyloxy, loweralkoxyloweralkyl, halogen, $-CF_3$, $-CN$,

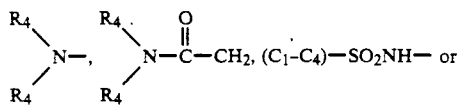

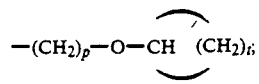

r is an integer of 1–4;
w is an integer of 1–3;
p is an integer of 1–3;
t is an integer of 2–5;
$R_4$ is hydrogen or lower alkyl; or a pharmaceutically acceptable salt thereof;
with the provisos that:
a) when A is

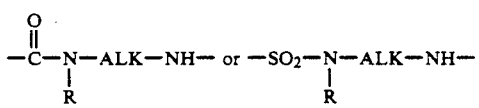

then
Q cannot be $(C_1-C_4)-SO_2NH-$;
b) Q cannot be ortho to the A attachment and when Q is $(C_1-C_4)-SO_2NH-$, it must be para to A;
c) when A is

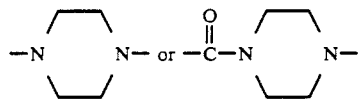

then x must be the integer 1;
d) when A is $-O-ALK-NH-$, then r cannot be the integer 1;
e) when x=0 then B cannot be

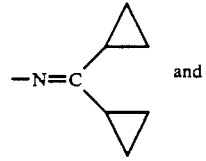 and f) when Q is $(C_1-C_4)-SO_2NH-$ and A is ALK then x must be the integer 1.

2. A compound of claim 1 where Q is $(C_1-C_4)-SO_2NH-$ and A is $-O-ALK-NH-$.

3. A compound of claim 1 where Q is

and A is $-O-ALK-NH-$.

4. A compound of claim 1 where A is

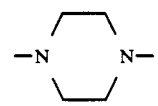

5. A compound of claim 1 which is N-[2-[[2-hydroxy-3-[4-(2-methoxyethyl)phenoxy]propyl]amino]ethyl]-4-(1H-imidazol-1-yl)benzamide.

6. A compound of claim 1 which is N-[4-[[2-hydroxy-3-(3-methylphenoxy)propyl]aminomethyl]phenyl]methanesulfonamide.

7. A compound of claim 1 which is N-[4-[[2-hydroxy-3-[4-(2-methoxyethyl)phenoxy]propyl]aminomethyl]phenyl]methanesulfonamide.

8. A compound of claim 1 which is 1-[[[4-(1H-imidazol-1-yl)phenyl]methyl]amino]-3-(2-methylphenoxy)-2-propanol.

9. A compound of claim 1 which is N-[2-[[2-hydroxy-3-(4-methoxyphenoxy)propylamino]ethyl]-4-(1H-imidazol-1-yl)benzamide.

10. A compound of claim 1 which is N-[2-[[2-hydroxy-3-(1-naphthalenyloxy)propyl]amino]ethyl]-4-(1H-imidazolyl-1-yl)benzamide.

11. A compound of claim 1 which is N-[2-[[2-hydroxy-3-[4-(methylsulfonyl)amino]phenoxy]propyl]amino]ethyl]-4-(1H-imidazol-1-yl)benzamide.

12. A compound of claim 1 which is 1-[2-hydroxy-3-(1-naphthalenyloxy)propyl]-4-[4-(methylsulfonyl)amino)benzoyl]piperazine.

13. A compound of claim 1 which is 1-[2-hydroxy-3-phenoxypropyl]-4-[4-[(methylsulfonyl)amino]benzoyl]piperazine.

14. A compound of claim 1 which is 1-[2-hydroxy-3-[4-(2-methoxyethyl)phenoxy]propyl]-4-[4-[(methylsulfonyl)amino]benzoyl]piperazine.

15. A compound of claim 1 which is N-[4-[(2-hydroxy-3-phenoxypropyl)aminomethyl]phenyl]methanesulfonamide.

16. A compound of claim 3 which is dicyclopropylmethanone O-[2-hydroxy-3-[[2-[4-(1H-imidazol-1-yl)phenoxy]ethyl]amino]propyl]oxime.

17. A compound of claim 3 which is 1-[[2-[4-(1H-imidazol-1-yl)phenoxy]ethyl]amino]-3-(3-methylphenoxy)-2-propanol.

18. A compound of claim 3 which is N-[4-[1-hydroxy-2-[[2-[4-(1H-imidazol-1-yl)phenoxy]ethyl]amino]ethyl]phenyl]methanesulfonamide.

19. A compound of claim 3 which is (R)-N-[4-[1-hydroxy-2-[[2-[4-(1H-imidazol-1-yl)phenoxy]ethyl]amino]ethyl]phenyl]methanesulfonamide.

20. A compound of claim 3 which is 1-[[2-[4-(1H-imidazol-1-yl)phenoxy]ethyl]amino]-3-[4-(2-methoxyethyl)phenoxy]-2-propanol.

21. A compound of claim 3 which is 4-[3-[[2-[4-(1H-imidazol-1-yl)phenoxy]-1,1-dimethylethyl]amino]-2-hydroxypropoxy]benzeneacetmide.

22. A compound of claim 3 which is N-[4-[2-hydroxy-3-[[2-(1H-imidazol-1-yl)phenoxy]ethyl]amino]propoxy]phenyl]methanesulfonamide.

23. A compound of claim 3 which is (S)-N-[4-[2-hydroxy-3-[[2-[4-(1H-imidazol-1-yl)phenoxy]ethyl]amino]propoxy]phenyl]methanesulfonamide.

24. A compound of claim 3 which is N-[4-[2-hydroxy-3-[[2-[4-(1H-imidazol-1-yl)phenoxy]-1,1-dimethylethyl]amino]propoxy]phenyl]methanesulfonamide.

25. A compound of claim 3 which is 1-[[2-[4-(1H-imidazol-1-yl)phenoxy]ethyl]amino]-3-phenoxy-2-propanol.

26. A compound of claim 3 which is α-[[2-[4-(1H-imidazol-1-yl)phenoxy]ethyl]aminomethyl]-3-methoxybenzenemethanol.

27. A compound of claim 4 which is N-[4-[4-[2-hydroxy-3-(3-methylphenoxy)propyl]piperazin-1-yl]phenyl]methanesulfonamide.

28. A compound of claim 4 which is N-[4-[4-[2-hydroxy-3-(2-methylphenoxy)propyl]piperazin-1-yl]phenyl]methanesulfonamide.

29. A compound of claim 4 which is (S)-N-[4-[4-[2-hydroxy-3-(2-methylphenoxy)propyl]piperazin-1-yl]phenyl]methanesulfonamide.

30. A compound of claim 4 which is N-[4-[4-[2-hydroxy-3-[(5,6,7,8-tetrahydro-5-oxo-1-naphthalenyl)oxy]propyl]-1piperazinyl]phenyl]methanesulfonamide.

31. A compound of claim 4 which is N-[4-[4-[3-[[[bis(cyclopropyl)methyl]imino]oxy]-2-hydroxypropyl]piperazin-1-yl]phenyl]methanesulfonamide.

32. A compound of claim 4 which is N-[4-[4-(2-hydroxy-3-phenoxypropyl)piperazin-1-yl]phenyl]methanesulfonamide.

33. A compound of claim 4 which is N-[4-[4-[2-hydroxy-3-[4-(2-methoxyethyl)phenoxy]propyl]piperazin-1-yl]phenyl]methanesulfonamide.

34. A compound of claim 4 which is 4-[2-hydroxy-3-[4-[4-[(methylsulfonyl)amino]phenyl]piperazin-1-yl]propoxy]-benzeneacetamide.

35. The method of treating arrhythmias in a mammalian host which comprises administering to said host a non-toxic effective amount of a compound of claim 1.

36. A pharmaceutical composition comprising a non-toxic amount of a compound of claim 1 together with a non-toxic pharmaceutically acceptable carrier.

* * * * *

UNITED STATES PATENT AND TRADEMARK OFFICE
CERTIFICATE OF CORRECTION

PATENT NO. : 5,051,423       Page 1 of 6
DATED : September 24, 1991
INVENTOR(S) : Randall E. Lis, et al.

It is certified that error appears in the above-identified patent and that said Letters Patent is hereby corrected as shown below:

Column 3, line 62

"2hydroxypropyl]" should read
--- 2-hydroxypropyl] ---

Columns 11 & 12, Scheme D

 should read

Column 20, line 33

"B-adrenergic blocking" should read
--- β-adrenergic blocking ---

Column 22, line 60

"and 21.0 9" should read
--- and 21.0g ---

UNITED STATES PATENT AND TRADEMARK OFFICE
CERTIFICATE OF CORRECTION

PATENT NO. : 5,051,423
DATED : September 24, 1991
INVENTOR(S) : Randall E. Lis, et al.

It is certified that error appears in the above-identified patent and that said Letters Patent is hereby corrected as shown below:

Column 23, line 13

"1 4-(4-nitrophenyl)" should read
--- 4-(4-nitrophenyl) ---

Column 23, line 46 & 47

"in 100 mL of anhydride in 50 mL of acetonitrile"
    should read
--- in 100 mL of acetonitrile add 6.49g (37 mmoL) of methanesulfonic anhydride in 50 mL of acetonitrile ---

Column 24, line 5

"3.48 (m,B)" should read
--- 3.48 (m,8) ---

Column 24, line 13

"a solution of 39.5 9" should read
--- a solution of 39.5g ---

Column 25, line 45

"To a solution of 7.95 9" should read
--- To a solution of 7.95g ---

UNITED STATES PATENT AND TRADEMARK OFFICE
CERTIFICATE OF CORRECTION

PATENT NO. : 5,051,423

DATED : September 24, 1991

INVENTOR(S) : Randall E. Lis, et al.

It is certified that error appears in the above-identified patent and that said Letters Patent is hereby corrected as shown below:

Column 27, line 65

"treat with 15 9" should read
--- treat with 15g ---

Column 31, line 68

"10.50 (br s,1)" should read
--- 10.50 (br s,1) ppm. ---

Column 32, line 35

"3.11-3.35 (m,B)" should read
--- 3.11-3.35 (m,8) ---

Column 32, line 44

"solution of 12.0 9" should read
--- solution of 12.0g ---

Column 33, line 3

"8.5 (b 3) 10.05 (b1) ppm." should read
--- 8.5 (br s,3), 10.05 (br s,1) ppm. ---

UNITED STATES PATENT AND TRADEMARK OFFICE
CERTIFICATE OF CORRECTION

PATENT NO. : 5,051,423

DATED : September 24, 1991

INVENTOR(S) : Randall E. Lis, et al.

It is certified that error appears in the above-identified patent and that said Letters Patent is hereby corrected as shown below:

Column 33, line 43

"Dissolve 3.89" should read
--- Dissolve 3.8g ---

Column 33, line 47

"with 0.85 9" should read
--- with 0.85g ---

Column 35, line 10

"2.9-4.2 (br,1 & $N_2O$)" should read
--- 2.9-4.2 (br,1 & $H_2O$) ---

Column 36, line 10

"8.9 (br t,l)" should read
--- 8.9 (br t,1) ---

Column 36, line 19

"3.14 9 (17.3 mmoL)" should read
--- 3.14g (17.3 mmoL) ---

UNITED STATES PATENT AND TRADEMARK OFFICE
CERTIFICATE OF CORRECTION

PATENT NO. : 5,051,423          Page 5 of 6
DATED     : September 24, 1991
INVENTOR(S) : Randall E. Lis, et al.

It is certified that error appears in the above-identified patent and that said Letters Patent is hereby corrected as shown below:

Column 39, line 12

"propylamino]" should read
    --- propyl]amino] ---

Column 39, line 19

"(methylsulfonyl)" should read
    --- [(methylsulfonyl) ---

Column 40, line 3

"benzeneacetimide" should read
    --- benzeneacetamide ---

UNITED STATES PATENT AND TRADEMARK OFFICE
CERTIFICATE OF CORRECTION

PATENT NO. : 5,051,423
DATED : September 24, 1991
INVENTOR(S) : Randall E. Lis, et al.

It is certified that error appears in the above-identified patent and that said Letters Patent is hereby corrected as shown below:

Column 40, line 5

"-3-[[2-(1H-imidazol" should read
--- -3-[[2-[4-(1H-imidazol ---

Column 40, line 30

"propyl]-1piperazenyl]" should read
--- propyl]-1-piperazenyl] ---

Signed and Sealed this

Twenty-sixth Day of October, 1993

Attest:

BRUCE LEHMAN

Attesting Officer

Commissioner of Patents and Trademarks